US010183053B1

(12) United States Patent
Rosen

(10) Patent No.: US 10,183,053 B1
(45) Date of Patent: Jan. 22, 2019

(54) MULTI-COMPONENT FORMULATIONS

(71) Applicant: Gene S. Rosen, Miami, FL (US)

(72) Inventor: Gene S. Rosen, Miami, FL (US)

( * ) Notice: Subject to any disclaimer, the term of this patent is extended or adjusted under 35 U.S.C. 154(b) by 0 days.

(21) Appl. No.: 15/626,260

(22) Filed: Jun. 19, 2017

(51) Int. Cl.
| | | |
|---|---|---|
| *A61K 31/10* | (2006.01) | |
| *A61K 36/81* | (2006.01) | |
| *A61K 31/7004* | (2006.01) | |
| *A61K 31/7016* | (2006.01) | |
| *A61K 36/82* | (2006.01) | |
| *A61K 31/7048* | (2006.01) | |

(52) U.S. Cl.
CPC .............. *A61K 36/81* (2013.01); *A61K 31/10* (2013.01); *A61K 31/7004* (2013.01); *A61K 31/7016* (2013.01); *A61K 31/7048* (2013.01); *A61K 36/82* (2013.01)

(58) Field of Classification Search
None
See application file for complete search history.

(56) References Cited

U.S. PATENT DOCUMENTS

| | | | |
|---|---|---|---|
| 4,780,456 | A | 10/1988 | Pistolesi |
| 5,516,526 | A | 5/1996 | DeLa Torre |
| 5,948,443 | A | 9/1999 | Riley et al. |
| 6,541,045 | B1 | 4/2003 | Charters et al. |
| 7,151,088 | B2 | 12/2006 | Moessler et al. |
| 7,238,373 | B2 | 7/2007 | Meyrowitz |
| 7,927,631 | B2 | 4/2011 | Phillips |
| 8,343,517 | B1 | 1/2013 | Bezzek |
| 8,491,889 | B1 | 7/2013 | Calton et al. |
| 8,609,629 | B2 | 12/2013 | Giordano et al. |
| 9,446,100 | B2 | 9/2016 | Holstein et al. |
| 9,655,942 | B2 | 5/2017 | Taal et al. |
| 9,682,048 | B1 * | 6/2017 | Rosen .................... A61K 31/10 |
| 2004/0241256 | A1 | 12/2004 | Ehrenpreis |
| 2006/0216251 | A1 | 9/2006 | Morariu |
| 2006/0251750 | A1 | 11/2006 | Tabor |
| 2007/0269454 | A1 | 11/2007 | Maeda et al. |
| 2008/0213401 | A1 | 9/2008 | Smith |
| 2009/0312273 | A1 * | 12/2009 | De La Torre .......... A61K 31/10 514/23 |
| 2009/0326275 | A1 | 12/2009 | DiMauro |
| 2010/0197795 | A1 | 8/2010 | Bettie, III et al. |
| 2011/0203585 | A1 * | 8/2011 | Cozean ................. A61M 16/06 128/203.12 |
| 2012/0263698 | A1 | 10/2012 | Barber |

FOREIGN PATENT DOCUMENTS

| | | | |
|---|---|---|---|
| WO | | 2007033082 A2 | 3/2007 |
| WO | | 2011123695 A1 | 10/2011 |
| WO | | 2012159092 A2 | 11/2012 |
| WO | WO 2018/027070 | * | 2/2018 |

OTHER PUBLICATIONS

Bitar V. et al. MSM and Green Tea Extract Reduced Oxidative Stress and Inflammation in an Ulcerative Coliitis. Asian J of Pharmaceutical and Clinical Research 6(Suppl 2)153-158, 2013. (Year: 2013).*
Putics et al: Zinc Supplementation Boosts the Stress Response in the Elderly: Hsp70 Status is Linked to Zinc Availability in Peripheral Lymphocytes. Exp Gerontol. May 2008; 43(5):452-61. (Abstract Only).
Qin et al: Cinnamon: Potential Role in the Prevention of Insulin Resistance, Metabolic Syndrome and Type 2 Diabetes. Journal of Diabetes Science and Technology. May 2010; 4(3):685-693. (Abstract and Complete Article).
Qin et al: Neuronal SIRTI Activation as a Novel Mechanism Underlining the Prevention of Alzheimer's Disease Amyloid Neuropathology by Calorie Restriction. Journal of Biological Chemistry Jun. 2006. Abstract and Poster.
Qiu et al: Is Low Blood Pressure a Risk Factor for Dementia and Alzheimer's Disease in the Elderly? International Conference on Alzheimer's Disease 2006 Poster PI-232.
Ramassamy: Emerging Role OfPolyphenolic Compounds in the Treatment of Neurodegenerative Diseases: A Review of Their Intracellular Targets. European Journal of Pharmacology 2006 545:51-64. (pp. 51,52 and 60 Only).
Rathel et al: Activation of Endothelial Nitric Oxide Synthase by Red Wine Polyphenols: Impact of Grape Cultivars, Growing Area and the Vinification Process. Journal of Hypertension Mar. 2007;25(3):541-9. (Abstract Only).
Regoli et al: Quantification of Total Oxidant Scavenging Capacity of Antioxidants for Peroxynitrite, Peroxyl Radicals, and Hydroxyl Radicals. Toxicology and Applied Pharmacology 1999; 156:96-105. (p. 96 and One Unnumbered Page Only).
Reuter et al: Epigenetic Changes Induced by Curcumin and Other Natural Compound. Genes Nutrition. May 2011. 6(2) 93-108. (Abstract Only).
Richards et al: Higher Serum Vitamin D Concentrations are Associated with Longer Leukocyte Telomere Length in Women. American Journal of Clinical Nutrition. Nov. 2007; 86(5):1420-1425. (Abstract Only).
Rickard et al: The Effect of Music on Cognitive Performance: Insight From Neurobiological and Animal Studies. Behavior Cognition Neuroscience Review. Dec. 2005; 4 (4) 235-61. (Abstract Only).
Ridley: Connecting the Pieces of the Alzheimer's Puzzle. Wall Street Journal 2010.
Rocca: Ovary Removal Surgery Elevates Risk for Dementia Mayo Clinic Release Apr. 5, 2006.
Roche Personalised Healthcare—In Brief. F. Hoffmann-La Roche AG. Dec. 2010.

(Continued)

*Primary Examiner* — Ralph J Gitomer

(74) *Attorney, Agent, or Firm* — Thrive IP®; Jeremy M. Stipkala

(57) ABSTRACT

Multi-component formulations comprise methylsulfonylmethane, fructose 1,6-diphosphate, and just one of trehalose, green tea extract, ashwagandha, and rutin, or a combination thereof. Multi-component formulations can prevent, delay, or treat cognitive decline, Alzheimer's disease, and other dementias.

13 Claims, 11 Drawing Sheets

(56) References Cited

OTHER PUBLICATIONS

Rodrigues et al: Total Oxidant Scavenging Capacity of Euterpe Oleracea Mart. (acai) Seeds and Identification of their Polyphenolic Compounds. Journal of Agricultural Food Chemistry. Jun. 2006; 54 (12):4162-7. (Abstract Only).
Rosen et al: Patterns of AB Accumulation in Alzheimer's and Aged Primate Brain. International Conference on Alzheimer's Disease 2006. Poster P2-005.
Rosen et al: Tauopathy with Paired Helical Filaments in an Aged Chimpanzee. The Journal of Comparative Neurology. May 2008. 509(3):259-270. (Abstract Only).
Rusanen et al: Heavy Smoking in Midlife and Long-Term Risk of Alzheimer Disease and Vascular Dementia. Archives of Internal Medicine Feb. 2011; 171 (4):333-339. (Abstract Only).
Saw et al: Synergistic Anti-Inflammatory Effects of Low Doses of Curcumin in Combination with Polyunsaturated Fatty Acids: Docosahexaenoic Acid or Eicosapentaenoic Acid. Biochemical Pharmacology Feb. 2010; 79 (3):421-430. (Abstract Only).
Scarmeas et al: Mediterranean Diet and Risk for Alzheimer's Disease. Annals of Neurology Jun. 2006; 59 (6):912-921. (Abstracts Only).
Sharma et al: Effect of Alpha Lipoic Acid, Melatonin and Trans Resveratrol on Intracerebroventricular Streptozotocin Induced Spatial Memory Deficit in Rats. Indian Journal of Physiology. Oct. 2005; 49(4):395-402. (Abstract Only).
Shaw: Fitness: Body and Mind. Harvard Magazine. Nov.-Dec. 2010, pp. 12-13.
Shaw: Head to Toe—Daniel Lieberman Tracks the Evolution of the Human Head. Harvard Magazine. Jan.-Feb. 2011, pp. 25, 27-29.
Shaywitz et al: Drug Research Needs Serendipity. Financial Times.
Shukitt-Hale et al: Walnuts can improve motor and cognitive function in aged rats. Society for Neuroscience 2007. Poster N24. (Abstract Only).
Siemers: Disease Modification: Will We Know It When We See It? International Conference on Alzheimer's Disease 2008. Presentation S2-04-02. (Abstract Only).
Silva: Nanotechnology Approaches to Crossing the Blood-Brain Barrier and Drug Delivery to the CNS. BMC Neuroscience. Dec. 2008; 9(Suppl)3:S4. (Complete Article and Abstract).
Singh et al: Allopregnanolone Reverses the Learning and Memory Deficits of Adult Triple Transgenic Alzheimer's Disease Mice. Society for Neuroscience 2008. Poster AA13. (Abstract Only).
Solfrizzi et al: Alcohol Consumption, Mild Cognitive Impairment, and Progression to Dementia. Neurology. May 2007; 68(21 ):1790-9. (Abstract Only).
Song et al: Hypoxia Facilitates Alzheimer's Disease Pathogenesis. International Conference of Alzheimer's Disease 2006 Poster P4-I 04.
Sowell et al: Assessing Immune-Related Oxidative Stress and Proteomics in a Mouse Model of Alzheimer's Disease. International Conference of Alzheimer's Disease 2008, Poster P4-177. (Abstract Only).
Spencer: The Impact of Fruit Flavonoids on Memory and Cognition. British Journal of Nutrition (2010), 104:S40-S47.
Steel: Alzheimer's Disease May not be a Disease at All: BMJ Jun. 16, 2006. (E-mail).
Suh et al: Pharmacological characterization of orally active cholinesterase inhibitory activity of *Prunus persica* L. Batsch in rats. Journal of Molecular Neuroscience. 2006; 29(2):101-7. (Abstract Only).
Tabet et al: Endogenous Antioxidant Activities in Relation to Concurrent Vitamins A, C, and E Intake in Dementia. International Psychogeriatrics. Mar. 2002; 14(1):7-15. (Abstract Only).
Tatzelt et al: Chemical Chaperones Interfere with the Formation of Scrapie Prion Protein. EMBO Journal Dec. 1996; 15(23):6363-6373. (Abstract Only).
Tchantchou et al: Dietary Supplementation with Apple Juice Concentrate Alleviates the Compensatory Increase in Glutathione Synthase Transcription and Activity that Accompanies Dietary- and Genetically-Induced Oxidative Stress. Journal of Nutritional Health & Aging. 2004; 8(6):492-6. (Abstract Only).
Teiten et al: Induction of Heat Shock Response by Curcumin in Human Leukemia Cells. Cancer Letters Jul. 2009; 279 (2):I45-54. (Abstract Only).
Terracciano et al: Personality and Resilience to Alzheimer's Disease Neuropathology: A Prospective Autopsy Study. Neurobiology of Aging Oct. 2012; (Abstract Only).
Tohda et al: Kihi-To, a Herbal Traditional Medicine, Improves Abeta (25-35)—Induced Memory Impairment and Losses of Neurites and Synapses. BMC Complementary and Alternative Medicine. Aug. 2008; 8:49. (Abstract Only).
Tucker et al: High Homocysteine and Low B Vitamins Predict Cognitive Decline in Aging Men: the Veterans Affairs Normative Aging Study. American Journal of Clinical Nutrition Sep. 2005; 82(3), 627-635. (Abstract Only).
Turner et al: Amyloid-Degrading Enzymes. (p. 7 Only).
U.S. Department of Health and Human Services, Food and Drug Administration, Center for Drug Evaluation and Research (COER): Guidance for Industry Codevelopment of Two or More Unmarketed Investigational Drugs for Use in Combination. Dec. 2010.
U.S. Department of Health and Human Services, Food and Drug Administration, Center for Drug Evaluation and Research (CDER): Guidance for Industry Codevelopment of Two or More Unmarketed Investigational Drugs for Use in Combination DRAFT Guidance. Dec. 2010. Federal Register 75:240:78259.
Valdez et al: Attenuation of Age Related Changes in Mouse Neuromuscular Synapses by Caloric Restriction and Exercise. Proceedings of the National Academy of Sciences Aug. 2010; 17; I 07 (33):14863-14868. (Abstract Only).
Vellas: Recommendations and Outcomes of Disease Modifying Drugs. International Conference on Alzheimer's Disease 2008. Presentation S2-04-01. (Abstract Only).
Venkataraman et al: Essential or Toxic? The Two Faces of the Abeta42 Peptide. International Conference on Alzheimer's Disease 2008. Poster P4-233. (Abstract Only).
Voelker: Guideline: Dementia Drugs' Benefits Uncertain. JAMA Apr. 2008. 299(15):1763.
Vogel: Do Jumping Genes Spawn Diversity? Science. Apr. 2011. vol. 332, pp. 300-301.
Vosler et al: Calpain-mediated Signaling Mechanisms in Neuronal Injury and Neurodegeneration. Molecular Neurobiology. Aug. 2008; 38( I ):78-100. (Abstract Only).
Wang: Alzheimer Diagnosis Possible With Scan. Wall Street Journal. Apr. 9, 2012.
Wen et al: Nmnat Exerts Neuroprotective Effects in Dendrites and Axons. Molecular and Cellular Neurosciences. Sep. 2011; 48(1):1-8. Epub May 9, 2011. (Abstract Only).
Whitehouse et al: Is Alzheimer's Disease an Outmoded Concept?—Putting the Patient and the Science First. International Conference on Alzheimer's Disease 2008. Poster PI-383. (Abstract Only).
Wieten et al: HSP70 expression and induction as a readout for detection of immune modulatory components in food. Cell Stress and Chaperones (2010) 15:25-37. (pp. 25-33 Only).
Wilson et al: Chronic Distress and Incidence of Mild Cognitive Imperilment. Neurology Jun. 2007; 68(24): 2085-2092. (Abstract Only).
Windisch et al: Role of Alpha-Synuclein in Neurodegenerative Diseases: A Potential Target for New Treatments Strategies? Neurodegenerative Diseases 2008; 5:218-221.
Wolfe et al: Cellular Antioxidant Activity of Common Fruits. Journal of Agricultural and Food Chemistry. Jul. 2008.
Wu et al: Hematopoietic Effect of Fractions from the Enzyme—Digested Colla Corii Asini on Mice with 5-Flourouracil Induced Anemia. American Journal of Chinese Medicine 2007; 35(5):853-66. (Abstract Only).
Xie: Changing Mind to Match the Feature of TCM for Developing Chromatographic Fingerprint to Assess the Quality of Herbal Medicine. Medicine in the 21st Century Tri-Conference & Bio-Forum 2004. Shanghai, China. pp. 108-109.
Yang et al: Coenzyme QIO Attenuates Hyperphosphorylation of Tau With Up-Regulation of AKT Signaling in the Aged Transgenic Mice

(56) References Cited

OTHER PUBLICATIONS with Alzheimer Presenilin 1 Mutation. International Conference on Alzheimer's Disease 2008. Poster P2-158. (Abstract Only).
Yao et al: Effects of Ejiao (Colla Corii Asini) on the Hemodynamics, Hemorheology and Microcirculation During Endotoxin Shock in Dogs. Zhongguo Zhong Yao Za Zhi. Jan. 1989; 14(1):44-6, 64. (Abstract Only).
Yuede et al: Effects Forced Versus Voluntary Exercise on Cognitive Deficits in Tg2576 Mice. International Conference on Alzheimer's Disease 2006, Poster PI-047. (Abstract Only).
Yurko-Mauro et al: Beneficial Effects of Docosahexaenoic Acid on Cognition in Age-Related Cognitive Decline. Alzheimer's & Dementia 2010:1-9.
Zamiska: Dueling Therapies: Is a Shotgun Better than a Silver Bullet. Wall Street Journal. Mar. 2, 2007.
Zelinski et al: The Impact Study: a Randomized Controlled Trial of a Brain Plasticity-Based Training Program for Age-Related Cognitive Decline. Society for Neuroscience 2007. Poster.
Zhai et al: NAD Synthase NMNAT Acts as a Chaperone to Protect Against Neurodegeneration. Nature Apr. 2008; V452:887-891.
Zhou et al: Clinical Study on Effect of Shenyin Oral Liquid in Treating Mild Cognitive Impairment. Zhongguo Zhong Xi Yi Jie He Za Zhi Sep. 2007; 27(9):793-5. (Abstract Only).
Zoladz et al: Cognitive Enhancement Through Stimulation of the Chemical Senses. North American Journal of Psychology 2005; 7(1). (First Page Only).
Un-Published Co-Pending U.S. Appl. No. 15/499,440, filed Apr. 27, 2017 (91 pages).
Cooper: Biotin Deficiency and Sodium-Dependent Multi-Vitamin Transporter Dysregulation Triggers the Alzheimer's Cascade. International Conference on Alzheimer's Disease 2008: Abstract and Poster P4-418.
Craik et al: Delaying the Onset of Alzheimer's Disease: Bilingualism as a Form of Cognitive Reserve. Neurology Nov. 2010; 75(19):1726-9. (Abstract Only).
Cullen et al: Microvascular Pathology in the Aging Human Brain: Evidence that Senile Plaques are Sites of Microhaemorrhages. Neurobiology of Aging 27 (2006) 1786-1796.
Curtis et al: Human Neuroblasts Migrate to the Olfactory Bulb via a Lateral Ventricular Extension. Science. Feb. 2007. (Abstract Only).
Dai et al: Abnormal Regional Cerebral Blood Flow in Cognitively Normal Elderly Subjects with Hypertension. Stroke Feb. 2008; 39:1-6.
Dartigues: Prodromal Alzheimer's Disease: Data from the PAQUID Study. International Conference of Alzheimer's Disease 2009, Presentation S4-02-04. (Abstract Only).
Das: Folic Acid and Polyunsaturated Fatty Acids Improve Cognitive Function and Prevent Depression, Dementia, and Alzheimer's Disease—But How and Why? Prostaglandins Leukot Essent Fatty Acids. Jan. 2008; 78(1):11-9. (Abstract Only).
De Lau et al: Folate Levels and Cognitive Performance. International Conference on Alzheimer's Disease 2006 Poster PI-205.
Dede et al: Endothelial Dysfunction and Alzheimer's Disease. International Conference on Alzheimer's Disease 2006 Poster P4-105.
De La Torre: Alzheimer Disease as a Vascular Disorder. Stroke 2002. 33:1152-1162.
De La Torre: Alzheimer's Disease is Incurable but Preventable. Journal of Alzheimer's Disease 2010.
De La Torre et al: Inhibition of Vascular Nitric Oxide After Rat Chronic Brain Hypoperfusion: Spatial Memory and Immunocytochemical Changes. Journal of Cerebral Blood Flow & Metabolism (2005) 25, 663-672.
De La Torre et al: Reversal of Ischemic-Induced Chronic Memory Dysfunction in Aging Rats with a Free Radical Scavenger-Glycolitic Intermediate Combination. Brain Research 1998; 779:285-288. (First Page Only).
De La Torre: Vascular Risk Factor Detection and Control May Prevent Alzheimer's Disease. Aging Research Reviews 2010.9:218-22. (First Page Only).

Department of Veterans Affairs: A Randomized, Clinical Trial of Vitamin E and Memantine in Alzheimer's Disease (TEAM-AD). Oct. 2005.
Dragicevic et al: Green Tea Epigallocatechin-3-Gallate (EGCG) and Other Flavonoids Reduce Alzheimer's Amyloid Induced Mitochondrial Dysfunction. Journal of Alzheimer's Disease 26 (2011) 507-521. (pp. 507-509 only).
Du et al: The Effect of Moxibustion on Spatial Memory of Aging Rats and the Underlying Mechanisms. International Conference on Alzheimer's Disease 2006. Poster P4-415.
Ebewe Pharma Ges, Investigator's Brochure, Cerebrolysin in Dementia. May 2003. (Cover Only).
Eckert et al: Plant Derived Omega-3 Fatty Acid Modulate Fatty Acid Composition in the Brain and Provide Neuroprotective Properties. Society for Neuroscience. 2008. Poster MI 0. (Abstract Only).
Egleton et al: Development of Neuropeptide Drugs that Cross the Blood Brain Barrier. NeuroRx Jan. 2005; 2(1):44-53. (pp. 44 and 50 Only).
Fackelmann: 18% of All Boomers Expected to Develop Alzheimer's. USA Today Mar. 18, 2008.
Frautschy et al: What was lost in translation in the DHA trial is whom you should intend to treat. Alzheimer's Research & Therapy. 2011, 3:2.
Frey II: Bypassing the Blood-Brain Barrier with Intranasal Delivery to Treat Alzheimer's Disease and Related Disorders. Poster No. S3-04-03.
Gabryelewicz et al: Conversion to Dementia Over a Five Year Period Among Patients with Mild Cognitive Impairment in Polish Follow-Up Study. International Conference of Alzheimer's Disease 2008 Poster PI-189. (Abstract Only).
Gao et al: Selenium and Cognitive Function in Rural Elderly Chinese. International Conference on Alzheimer's Disease 2006 Poster P3-124.
Goldsmith: Treatment of Alzheimer's Disease by Transposition of the Omentum. Annals of The New York Academy of Science 2002. 977:456-467. (p. 454 Only).
Grundman et al: Antioxidant Strategies for Alzheimer's Disease. Proceedings of Nutrition Society May 2002; 61 (2)191-202. (Abstract Only).
Gureviciene et al: Amyloid Plaques Confer Neuroprotection Against Exogenous A Oligomers. Society for Neuroscience 2012, Program 748.16/E9. (Abstract Only).
Guskiewicz et al: Association between Recurrent Concussion and Late-Life Cognitive Impairment in Retired Professional Football Players. Neurosurgery Oct. 2005; 57 (4):719-26. (Abstract Only).
Hanson et al: Intranasal Delivery Bypasses the Blood-Brain Barrier to Target Therapeutic Agents to the Central Nervous System and Treat Neurodegenerative Disease. BMC Neuroscience. Dec. 2008; 9 Suppl 3:S5. (Abstract Only).
Hartman et al: Pomegranate Juice Decreases Amyloid Load and Improves Behavior in a Mouse Model of Alzheimer's Disease. Neurobiol Dis. Sep. 27, 2006 (Abstract Only).
Heo et al: Protective Effects of Quercetin and Vitamin C Against Oxidative Stress-Induced Neurodegeneration. Journal of Agricultural Food Chemistry. Dec. 2004; 52(25):7514-17. (Abstract Only).
Herrera et al: Human Photosynthesis and its Impact on Alzheimer's and Other Neurodegenerative Diseases. International Conference on Alzheimer's Disease 2008. Poster.
Herrmann et al: Uncovering the Proteomic Basis of Mitochondrial Dysfunction in Relation to Alzheimer's Disease. Society for Neuroscience 2012, Program 747.09/048. (Abstract Only).
Ho et al: Anti-Aging Herbal Medicine-How and Why Can They be Used in Aging Associated Neurodegenerative Diseases? Aging Research Reviews 9 (2010) 354-362.
Ho et al: Isolation and Characterization of Grape-Derived Polyphenolic Extracts with Abeta—Lowering Activity That Could be Developed for Alzheimer's Disease. Society for Neuroscience 2007. Program 548.7. (Abstract Only).
Holtzman et al: Alzheimer's Disease: The Challenge of the Second Century. Science Translational Medicine. Apr. 6, 2011; 3(77):77sr1. (pp. 1 and 12 Only).

(56) References Cited

OTHER PUBLICATIONS

Hotz: Tiny Gene Variations Can Even Alter Effect of the Pills We Take. Wall Street Journal Mar. 21, 2008.
Ignarro et al: Pomegranate Juice Protects Nitric Oxide Against Oxidative Destruction and Enhances the Biological Actions of Nitric Oxide. Nitric Oxide. Sep. 2006; 15 (2):93-1 02. (Abstract and First Page Only).
Impact of a 5-Year Delayed Onset of AD Due to a Treatment Breakthrough. Alzheimer's Association Website Accessed Jun. 30, 2010.
Jacob et al: Pharmacology of Dimethyl Sulfoxide in Cardiac and CNS Damage. Pharmacological Reports 2009; 61 :225-235.
Jefferson et al.: Cardiac Function is Related to Maladaptive Brain Aging in Individuals with Mild Cognitive Impairment: Preliminary Results. International Conference on Alzheimer's Disease 2009 Poster.
Jeong et al: Environmental Enrichment Compensates the Effects of Stress on the Disease Progression in the Tg2576 Mice, an Alzheimer's Disease Model. Society for Neuroscience 2007. Poster M16. (Abstract Only).
Jicha et al: Omega-3 Fatty Acids: Potential Role in the Management of Early Alzheimer's Disease. Clinical Interventions in Aging. 2010:5 45-61.
Johns Hopkins School of Public Health: Alzheimer's Disease to Quadruple Worldwide by 2050. Public Health News Center. Jun. 10, 2007.
Jones et al: Variation in Placebo Decline Across a Decade of Alzheimer's Disease Trials. International Conference on Alzheimer's Disease 2008. Poster.
Kad et al: Collaborative Dynamic DNA Scanning by Nucleotide Excision Repair Proteins Investigated by Single-Molecule Imaging of Quantum-Dot-Labeled Proteins. Molecular Cell. Mar. 2010; 37(5):702-713. (Summary Only).
Kalt et al: Effect of Blueberry Feeding on Plasma Lipids in Pigs. British Journal of Nutrition Nov. 2007. (p. 1 of 9 Only).
Kamphuis et al: Can Nutrients Prevent or Delay Onset of Alzheimer's Disease? Journal of Alzheimer's Disease 20 (2010) 765-775.
Karaca et al: Ischemic Stroke in Elderly Patients Treated with a Free Radical Scavenger—Glycolytic Intermediate Solution: a Preliminary Pilot Trial. Neurological Research Jan. 2002; 24 (1):73-80. (Abstract and p. 73 Only).
English Translation of Russian Patent No. 2478376 (C1), "Pharmaceutical Composition Based on Vegetative DHA for Treating and Preventing Diseases of Joints," Konsortsium PIK, issued Apr. 10, 2013 (11 pages).
Codispoti et al: Longitudinal Brain Activity Changes in Asymptomatic Alzheimer Disease. Brain and Behavior 2012. (pp. 221-230).
Collins et al: Watermelon Consumption Increases Plasma Arginine Concentrations in Adults. Nutrition. Mar. 2007; 23(3):261-6. (Abstract Only).
Aggarwal et al: Curcumin: The Indian Solid Gold. Adv Exp Med Biol. 2007;595:1-75. (Abstract Only).
Aggarwal et al: Curcumin—Biological and Medicinal Properties. Turmeric: The Genus *Curcuma* 2006 Chapter 10. (pp. 297-298, 329-330 Only).
Ali et al: Dealing with Misfolded Proteins; Examining the Neuroprotective Role of Molecular Chaperones in Neurodegeneration. Molecules 2010;15:6859-6887. (pp. 6859-6874 Only).
Ali et al: Nicotinamide Mononucleotide Adenylyltransferase is a Stress Response Protein Regulated by the HFS/HIF I A {alpha} Pathway. Journal of Biological Chemistry May 20 II; 286(21):I9089-99. (Abstract Only).
Ali et al: NMNAT Suppresses Tau-Induced Neurodegeneration by Promoting Clearance of Hyperphosphorylated Tau Oligomers in a *Drosophila* Model of Tauopathy. Human Molecular Genetics. Sep. 30, 2011; 21(2):237-250. (Abstract Only).
Aliev et al: Brain Mitochondria as a Primary Target in the Development of Treatment Strategies for Alzheimer's disease. The International Journal of Biochemistry and Cell Biology 2009. (p. 1 only).

Alvarez et al: A 24-Week, Double-Blind Placebo-Controlled Study of Three Dosages of Cerebrolysin in Patients with Mild to Moderate Alzheimer's Disease. European Journal of Neurology Jan. 2006; 13(1):43-54. (Abstract Only).
Alvarez et al: Neuropeptide Dietary Supplement N-PEP-12 Enhances Cognitive Function and Activates Brain Bioelectrical Activity in Healthy Elderly Subjects. Methods Find Exp Clin Pharmacal. Sep. 2005; 27 (7):483-87. (Abstract Only).
Alzheimer'S Association: Changing the Trajectory of Alzheimer's Disease: A National Imperative. (3 pages).
Anderson: Chromium and Polyphenols from Cinnamon Improve Insulin Sensitivity. Proceedings Nutrition Society Feb. 2008; 67(1):48-53. (Abstract Only).
Andrew et al: Social Vulnerability Predicts Cognitive Decline in a Prospective Cohort of Older Canadians. International Conference on Alzheimer's Disease 2006 Poster P3-127.
Anselm et al: Grape Juice Causes Endothelium-Dependent Relaxation via a Redox-Sensitive Src- and Akt-Dependent Activation of eNOS. Cardiovascular Research 2007. Jan. 15;73(2):404-13. Epub Aug. 8, 2006. (Abstract Only).
A Randomized Double Blind, Placebo-Controlled Trial to Evaluate the Safety and Efficacy of New Therapy in Patients with Mild to Moderate Probable Alzheimer's Disease. JSW Life Sciences, Graz, Austria.
Arendash et al: Environmental Enrichment "Sessions" are Sufficient to Provide Cognitive Benefit to Impaired Alzheimer's Transgenic Mice Without Affecting Brain or Plasma AB Levels. International Conference on Alzheimer's Disease 2008. Poster P1-068. (Abstract Only).
Baker et al: Age-Related Learning Deficits Can be Reversible in Honeybees Apis mellifera. Exp Gerontol. Oct. 2012; 47(10):764-72 (Abstract Only).
Baker et al: Regional Overlap of Cerebral Glucose Metabolism at Rest and During List Learning for Older Insulin Resistant and Alzheimer Adults. International Conference on Alzheimer's Disease. Poster P2-224.
Banks: Developing Drugs That Can Cross the Blood-Brain Barrier: Applications to Alzheimer's Disease. BMC Neuroscience 2008. 9(Suppl)3:S2.
Bardutzky et al: Effects of Intravenous Dimethyl Sulfoxide on lschemia Evolution in a Rat Permanent Occlusion Model. Journal Cerebral Blood Flow Metabolism Aug. 2005; 25 (8):968-77. (Abstract Only).
Barger: Cooperative Ideas About Cooperative Strategies. Annals of The New York Academy of Science 2004; 1035:350-353. (pp. 350-352 Only).
Bates et al: Relationship between Cardiovascular Disease Risk Factors and Alzheimer's Disease AB Protein in Subjective Memory Complainers. International Conference on Alzheimer's Disease 2008 Poster PI-342. (Abstract Only).
Bauer et al: Photobiomodulation Attenuates CNS Oxidative Stress in an Animal Model of Diabetes. Society for Neuroscience 2008. Poster 26.
Baur et al: Resveratrol Improves Health and Survival of Mice on a High Calorie Diet. Nature. Nov. 2006. (Abstracts Only).
Beking et al: Flavonoids and Alzheimer's Disease Prevention; An Ecological Analysis of Potential Neuropotective Factors. International Conference on Alzheimer's Disease 2009. Poster.
Bin Li et al: Enhancement of Dentate Gyrus Neurogenesis and Associated Memory by a Neurotrophic Peptide. Jul. 28, 2008, Poster No. P2-445. (Abstract Only).
Blair et al: In Vivo Administration of Heat Shock Protein 27 Variants; Implications for tauopathies. Society for Neuroscience 2009, Program 600.3. (Abstract Only).
Bondy et al: Retardation of Brain Aging by Chronic Treatment with Melatonin. Annals of The New York Academy of Sciences 2004; 1035:197-215. (pp. 197 and 211 Only).
Brain Energizer: A Randomized, Double-Blind, Placebo-Controlled Trial, Changchung City 2nd Hospital, China 1997.
Camici et al: Dimethyl Sulfoxide Inhibits Tissue Factor Expression, Thrombus Formation, and Vascular Smooth Muscle Cell Activation. Circulation 2006; 114:1512-1521. (p. 1512 Only).

(56) References Cited

OTHER PUBLICATIONS

Cao et al: Caffeine Synergizes with Another Coffee Component to Increase Plasma GCSF: Linkage to Cognitive Benefits in Alzheimer's Mice. Journal of Alzheimer's Disease. 2011; 25(2):323-35. (Abstract Only).
Caprini et al: Mental Activity and Dementia Risk. International Conference on Alzheimer's Disease 2006 Poster P4-170.
Cavallucci et al: HSP70 Deregulation in a Mouse Model of Alzheimer's Disease: A Potential Mechanism for Early Synaptic Deficit. Society for Neuroscience 2009. Poster B117. (Abstract Only).
Chan et al: A Vitamin/Nutriceutical Formulation Improves Memory and Cognitive Performance in Community-Dwelling Adults without Dementia. Journal of Nutritional Health and Aging. 2010; 14(3) 224-30. (Summary Only).
Chan et al: Apple Juice Concentrate Maintains Acetylcholine Levels Following Dietary Compromise. Journal of Alzheimer's Disease. Aug. 2006; 9(3):287-91. (Abstract Only).
Chang et al: Development of Gouqizi (Lycium Barbarum) as Neuroprotective Agents. The University of Hong Kong, Aug. 2005. (pp. 1-4, 6, 7-9).
Chang et al: Medicinal and Nutraceutical Uses of Wolfberry in Preventing Neurodegeneration in Alzheimer's Disease. Recent Advances on Nutrition and the Prevention of Alzheimer's Disease. 2010; 169-185.
Chang et al: Significance of Molecular Signaling for Protein Translation Control in Neurodegenerative Diseases. Neuro-Signals 2007. 15:249-258. (pp. 249, 254 and 255 Only).
Chang et al: Use of Anti-Aging Herbal Medicine, Lycium barbarum, Against Aging Associated Diseases. What Do We Know So Far? Cell Mol Neurobiol Jul. 2007.
Chao et al: Dietary Oxyresveratrol Prevents Parkiansonian Mimetic 6-Hydroxydopamine Neurotoxicity. Free Radical Biology and Medicine 2008; 45:1019-1026. (First Page Only).
Chao et al: Novel Neuroprotective Effects of Oxyresveratrol Preventing 6-Hydroxydopamine—Induced Neurotoxicity: Antioxidant Activity and Up-Regulation of sirt1. Poster No. X5. Society for Neuroscience 2008. (Presentation Abstract).
Chauhan et al: Walnut Extract Inhibits the Fibrillization of Amyloid Beta-Protein, and Also Defibrillizes its Preformed Fibrils. Current Alzheimer Research. Aug. 2004; 1 (3):183-8. (Abstract Only).
Chen et al: New Therapies from Old Medicines. Nature Biotechnology. Oct. 2008; 26(10):1077-1083.
Chen: Regulatory Prospects of Botanical New Drugs. Medicine in the 21st Century Tri-Conference & Bio-Forum 2004. Shanghai, China. pp. 220-226.
Chiu et al: Up-regulation of Crystallins is involved in the neuroprotective effect of wolfberry on survival of retinal ganglion cells in rat ocular hypertension model. Journal of Cellular Biochemistry Mar. 2010; 110:311-320.
Chohan et al: Enhancement of Dentate Gyrus Neurogenesis, Dendritic and Synaptic Plasticity and Memory by Neurotrophic Peptide. Neurobiology of Aging Aug. 2011; 32(8):1420-34. (Abstract Only).
Clarke et al: Vitamin B-12, Holotranscobalamin and Risk of Cognitive Decline: 10-Year Follow-Up of the Oxford healthy Aging Project. International Conference on Alzheimer's Disease 2006 Poster P3-126.
Butawan et al.: Methylsulfonylmethane: Applications and Safety of a Novel Dietary Supplement, Nutritents 9, 290 (2017).
Cole et al: Brain age predicts mortality. Molecular Psychiatry (2017) 00, 1-8.
Cortes-Canteli et al: Fibrinogen and Altered Hemostasis in Alzheimer's Disease. National Institute of Health, J Alzheimers Dis. Author Manuscript, 2012; 32(3): 599-608.
Cummings et al: Alzheimer's disease drug development pipeline: 2017. Alzheimer's and Dementia: Translational Research & Clinical Interventions 3 (2017) 367-384.
R. Flaumenhaft: Protein disulfide isomerase as an antithrombotic target. Science Direct, Trends in Cardiovascular Medicine 23 (2013) 264-268.

Dar et al: Pharmacologic overview of Withania somnifera, the Indian Ginseng. Cellular and Molecular Life Sciences, (2015) 72:4445-4460.
Jack C. De La Torre: Alzheimer's Turning Point, A Vascular Approach to Clinical Prevention, (2016) p. 117.
Enzo Emanuele: Can Trehalose Prevent Neurodegeneration? Insights from Experimental Studies. Bentham Science Publishers, Current Drug Targets, (2014) 15, 000-000.
Friedman et al: Promoting Autophagic Clearance: Viable Therapeutic Targets in Alzheimer's Disease. The American Society for Experimental NeuroTherapeutics, Inc. 2014 (15 pages).
Du et al: Trehalose rescues Alzheimer's disease phenotypes in APP/PS1 transgenic mice: Royal Pharmaceutical Society, Journal of Pharmacy and Pharmacology, 65, (2013) 1753-1756.
Kim et al: MSM ameliorates HIV-1 Tat induced neuronal oxidative stress via rebalance of the glutathione cycle. Am J Transl Res 2015; 7(2):328-338.
Javed et al: Rutin Prevents Cognitive Impairments by Ameliorating Oxidative Stress and Neuroinflammation in Rat Model of Sporadic Dementia of Alzheimer Type. Neuroscience 210 (2012) 340-352.
Nelson et al: The Essential Medicinal Chemistry of Curcumin. ACS Publications, Journal of Medicinal Chemistry, 2017, 60, 1620-1637.
Pingali et al: Effect of standardized aqueous extract of Withania somnifera on tests of cognitive and psychomotor performance in healthy human participants. Pharmacognosy Res. (2014) Jan.-Mar.; 6(1): 12-18.
Kuboyama et al: Effects of Ashwagandha (Roots of Withania somnifera) on Neurodegenerative Diseases. The Pharmaceutical Society of Japan, Biol. Pharm. Bull. 37(6) 892-897 (2014).
Kruger et al: Autophagic degradation of tau in primary neurons and its enhancement by trehalose. Neurology of Aging 33 (2012) 2291-2305.
Liu et al: Trehalose differentially inhibits aggregation and neurotoxicity of beta-amyloid 40 and 42. Neurobiology of Disease 20 (2005) 74-81.
Vareed et al: Blood-Brain Barrier Permeability of Bioactive Withanamides Present in Withania somnifera Fruit Extract. Phytotherapy Research, Phytother. Res. 28 (2014) 1260-1264.
Wadhwa et al: Nootropic potential of Ashwagandha leaves: Beyond traditional root extracts. Neurochemistry International 95 (2016) 109-118.
Rao et al: Ayurvedic medicinal plants for Alzheimer's disease: a review. Alzheimers Res Ther. 2012; 4(3): 22, (14 pages).
Richards et al: Trehalose: a review of properties, history of use and human tolerance, and results of multiple safety studies. Food and Chemical Toxicology 40 (2002) 871-898.
Singer et al: Multiple Effects of Trehalose on protein Folding In Vitro and In Vivo. Molecular Cell, vol. 1, 639-648, Apr. 1998.
Dragicevic et al: Green Tea Epigallocatechin-3-Gallate (EGCG) and Other Flavonoids Reduce Alzheimer's Amyloid-Induced Mitochondrial Dysfunction. Journal of Alzheimer's Disease 26 (2011) 507-521.
Schmidt et al: Green tea extract enhances parieto-frontal connectivity during working memory processing. Psychopharmacology, Mar. 19, 2014 (10 pages).
Kaufman et al: Cognitive Decline in Alzheimer's disease: Impact of Spirituality, Religiosity and QOL. Neurology May 2007; 68(18):1509-1514. (Abstract Only).
Kennedy et al: Effects of Resveratrol on Cerebral Blood Flow Variables and Cognitive Performance in Humans: A Double-Blind, Placebo-Controlled, Crossover Investigation. American Journal of Clinical Nutrition Jun. 2010; (6):1590-7. (Abstract and Complete Article).
Kim et al: Alzheimer's Disease Drug Discovery from Herbs. Journal of Alternative and Complementary Medicine 2007; 13(3):333-340. (Abstract and Complete Article).
Kiraly et al: Traumatic Brain Injury and Delayed Sequelae: A Review—Traumatic Brain Injury and Mild Traumatic Brain Injury (Concussion) are Precursors to Later-Onset Brain Disorders, Including Early-Onset Dementia. Scientific World Journal Nov. 12, 2007; 7:1768-76. (Abstract Only).
Kivipelto et al: Obesity and Vascular Risk Factors at Midlife and the Risk of Dementia and Alzheimer Disease. Archives of Neurology Oct. 2005; 62 (10):1556-60. (Abstracts Only).

(56) References Cited

OTHER PUBLICATIONS

Klein et al: Grape-Enriched Diet Upregulates Transthyretin in Aged Mouse Brain: Potential Protection From Alzheimer's Disease? International Conference on Alzheimer's Disease 2007. Poster N27. (Abstract Only).
Kraus et al: Exercise Training, Lipid Regulation, and Insulin Action: A Tangled Web of Cause and Effect. Obesity (Silver Spring) Dec. 2009; 17 (N3S):S21-S26. (Abstract Only).
Krikorian et al: Blueberry Supplementation Improves Memory in Older Adults. Journal of Agricultural and Food Chemistry. Jan. 2010.
Ladiwala et al: Resveratrol Selectively Remodels Soluble Oligomers and Fibrils of Amyloid Abeta into Off-Pathway Conformers. J Bioi Chem. Jul. 2010; 285 (31):24228-37. (Abstract Only).
Laitinen et al: Fat Intake at Midlife and Cognitive Impairment Later in Life: A Population Based Study. International Conference on Alzheimer's Disease 2006. Poster P3-125.
Larson et al: Exercise is Associated with Reduced Risk for Incident Dementia Among Persons 65 Years of Age and Older. Annals of Internal Medicine Jan. 2006; 144 (2):73-81. (Abstract Only).
Lee et al: Perspectives on the Amyloid-B Cascade Hypothesis. Journal of Alzheimer's Disease 6 (2004) 137-145.
Li et al: Pharmacological Studies of Traditional Chinese Medicine to Treat Alzheimer's Disease. International Conference on Alzheimer's Disease 2006. Poster P4-273.
Liang: On Fingerprinting Techniques for Quality Control of TCM. Medicine in the 21st Century Tri-Conference & Bio-Forum 2004. Shanghai, China. pp. 76-78 and 87.
Ljungberg et al: CREB-Activity and nmnat2 Transcription are Down-Regulated Prior to Neurodegeneration, while NMNAT2 Over-Expression is Neuroprotective, in a Mouse Model of Human Tauopathy. Human Molecular Genetics. Oct. 25, 2011; 21(2):251-267. (Abstract Only).
Lombardo et al: Memory Preservation Diet for Reducing Risk and Slowing Progression of Alzheimer's Disease. International Conference on Alzheimer's Disease 2006. Poster P-157.
Lonsdorf et al: Neurological Understanding of Ayurvedic Medicine and its Application to Dementia Prevention. International Conference on Alzheimer's Disease 2006. Poster P-168.
Luchsinger et al: Relation of Diabetes to Mild Cognitive Impairment. International Conference on Alzheimer's Disease 2006. Poster P3-129.
Ma et al: Beta-Amyloid Oligomers Induce Phosphorylation of Tau and Inactivation of Insulin Receptor Substrate via c-Jun N-Terminal Kinase Signaling: Suppression by Omega 3 Fatty Acids and Curcumin. Journal of Neuroscience Jul. 2009; 29 (28):9078-9089. (Abstract and pp. 9078-9089).
Maczurek et al: Lipoic Acid as an Anti-Inflammatory and Neuroprotective Treatment for Alzheimer's Disease. Advance Drug Delivery Review. Jul. 2008. (Abstract Only).
Malin et al: Short-Term Blueberry-Enriched Diet Prevents and Reverses Object Recognition and Memory Loss in Aging Rats. Nutrition 27 (2011) 338-342. (First Page Only).
Mathews: Recent Cases Point to the Limitations of Animal Drug Tests. Wall Street Journal. Mar. 31, 2007.
Mattson et al: Neurohorrnetic Phytochemicals: Low Dose Toxins that Induce Adaptive Neuronal Stress Responses. Trends in Neuroscience. Sep. 2006; 29(11). (Incomplete).
Mawuenyega et al: Decreased Clearance of CNS—Amyloid in Alzheimer's Disease. Science Dec. 2010: 330:177.4.
McKinsey et al: Cerebral Perfusion in Alzheimer's Disease Using Dynamic Susceptibility Contrast MRI. International Conference of Alzheimer's Disease 2008, Poster P2-228. (Abstract Only).
Morillo et al: Obesity and Cognition in an Interdisciplinary Program to Treat Aged Women Obesity. International Conference on Alzheimer's Disease 2008. Poster P2-117. (Abstract Only).
Morris et al: Dietary Copper and High Saturated and trans Fat Intakes Associated with Cognitive Decline. Archives of Neurology Aug. 2006; 63:1083-1088. {Abstract Only).

Muldoon et al: Serum Phospholipid Docosahexaenoic Acid is Associated with Cognitive Functioning during Middle Adulthood. Journal of Nutrition. Feb. 24, 2010. (Summary Only).
Myung et al: Improvement of Memory by Dieckol and Phlorofucofuroeckol in Ethanol-Treated Mice: Possible Involvement of the Inhibition of Acetylcholinesterase. Archives of Pharmaceutical Research. Jun. 2005; 28(6):691-8. (Abstract Only).
Nabel et al: Demystifying DNA Demethylation. Science. Sep. 2011. 333(6047):1229-1230.
Napryeyenko et al: Ginkgo Biloba Special Extract in Dementia with Neuropsychiatric Features. A Randomized, Placebo-Controlled, Double-Blind Clinical Trial. Arzneimittelforschung 2007; 57( I ):4-11. (Abstract Only).
Neubauer et al: New Frontiers: Anti-Aging Properties of Hyperbaric Oxygen Therapy. (First Page Only).
Neuroscience Under Threat as Big Pharma Backs Off. Reuters News. Feb. 11, 2011.
Newman et al: Natural Products as Sources of New Drugs Over the Last 25 Years. Journal Natural Products 2007. 70:461-477. (p. 461 Only).
No Longer Treating Different Conditions Identically. Roche Nachrichten Oct. 2008.
O'Leary et al: Chemically Tuning Tau Fate Decisions with Chaperone Modulators. Society for Neuroscience 2009. Program 600.2. (Abstract Only).
Ownby et al: Depression and Risk for Alzheimer disease: systematic review, meta-analysis, and metaregression analysis. Archives of General Psychiatry May 2006; 63 (5):530-8. (Abstract Only).
Panickar: Beneficial Effect of Herbs, Spices, and Medicinal Plants on the Metabolic Syndrome, Brain, and Cognitive Function. Central Nervous System Agents in Medicinal Chemistry, 2013, vol. 13, No. 1 (pp. 1-17).
Parachikova et al: Formulation of a Medical Food Cocktail for Alzheimer's Disease. Beneficial Effects on Cognition and Neuropathology in a Mouse Model of the Disease. PLoS One. Nov. 2010; 5(1J):e14015.
Park et al: Methyl Salicylate is a Critical Mobile Signal for Plant Systemic Acquired Resistance. Science. Oct. 2007; 318:113-116.
Park: Alzheimer's Unlocked. Time Magazine. Oct. 25, 2010. pp. 53-59.
Pasinetti et al: Grape Seed Polyphenolic Extracts (GSPE) as a Potential Novel Treatment in Progressive Supranuclear Palsy: Experimental Approaches and Therapeutic Implications. Program No. 600.4. Society for Neuroscience 2009. (Presentation Abstract).
Passos et al: Feedback Between p21 and Reactive Oxygen Production Is Necessary for Cell Senescence. Molecular Systems of Biology. Feb. 2010; 6:347.
Patel et al: Getting into the Brain Approaches to Enhance Brain Drug Delivery. CNS Drugs 2009; 23(1):35-52.
Patel et al: True Healing Art of Alzheimer's by Holistic Homeopathy. International Conference of Alzheimer's Disease 2006. Poster PI-448.
Piau et al: Progress in the Development of New Drugs in Alzheimer's Disease. Journal of Nutrition, Health & Aging. 2011;15(1):45-57. (p. 45 Only).
Plumridge: Pharmaceutical Sector Remains Genetically Challenged. Wall Street Journal Jan. 2011.
Prasad et al: Multiple Antioxidants in the Prevention and Treatment of Neurodegenerative Disease: Analysis of Biologic Rationale. Current Opinion in Neurology Dec. 1999; 12 (6):761-770.
Presley et al: Acute Effect of a High Nitrate Diet on Brain Perfusion in Older Adults. Nitric Oxide. Oct. 2010. (Abstract Only).
Putics et al: Resveratrol Induces the Heat-Shock Response and Protects Human Cells From Severe Heat Stress. Antioxidant Redox Signal. Jan. 2008; 10(1 ):65-75. (Abstract Only).
Notice of Allowance dated Oct. 15, 2018, U.S. Appl. No. 15/499,440 (7 pages).
Non-Final Office Action dated Jul. 16, 2018, U.S. Appl. No. 15/499,440 (12 pages).
U.S. Appl. No. 15/499,440, filed Apr. 27, 2017 (91 pages).
Aggarwal et al; Potential therapeutic effects of Curcumin, the anti-inflammatory agent, against neurodegenerative, cardiovascular,

(56) References Cited

OTHER PUBLICATIONS pulmonary, metabolic, autoimmune and neoplastic diseases; The International Journal of Biochemistry & Cell Biology, (Jan. 2009) vol. 41, No. 1, (pp. 40-59).

* cited by examiner

MULTI-COMPONENT FORMULATIONS

FIELD OF INVENTION

This invention relates to compositions for administration to human or animal patients, and methods of preventing, delaying, and treating cognitive decline, Alzheimer's disease and other dementias, and other neurodegenerative diseases using those compositions.

BACKGROUND OF THE INVENTION

Alzheimer's disease ("AD") is believed to be a multifactorial degenerative disease rather than the result of a single malfunction or agent. Although AD is usually accompanied by the abnormal accumulation of extracellular deposits or plaques of β-amyloid protein (AB) and intracellular neurofibrillary tangles of tau protein (NFTs), extensive research has not isolated or identified a cause for the accumulation, nor shown that β-amyloid protein or NFTs are the cause rather than effect of AD. In fact, approximately 30 percent of AD patients have no AB plaques or NFTs at death, and approximately 30 percent of cognitively normal adults do have AB plaques and NFTs at death. AB plaques may even be protective against harmful soluble AB oligomers. Instead, clinical and epidemiological studies have identified numerous contributing factors to AD.

Many of the pathologic characteristics of AD, inflammation, oxidative stress, impaired cerebral blood flow and glucose utilization, result from body imbalances, including stress, obesity, and an overloaded immune system. In addition, AD has a lengthy, non-linear, accelerating, and degenerative prodromal time period with ample opportunity for preventive intervention, and about 95 percent of AD cases are sporadic late-onset.

However, no comprehensively-effective medicine or protocol has emerged for AD or other dementias. Yet it is estimated that about 44 million patients suffer from AD or a related dementia worldwide. Cognitive decline affects significantly more. New compositions designed on the growing understanding of neurobiochemistry, cognitive decline, AD, other dementias, and neurodegeneration in general are needed.

SUMMARY OF THE INVENTION

Unexpectedly, Applicant has invented certain compositions that can be used in the prevention, delay, and treatment of cognitive decline, such as, for example, in AD patients. Accordingly, some embodiments of the present invention relate to multi-component formulations comprising methylsulfonylmethane, fructose 1,6-diphosphate, and at least one of trehalose, green tea extract, ashwagandha, and rutin. In certain instances, the multi-component formulations comprise just one of trehalose, green tea extract, ashwagandha, and rutin.

Further embodiments relate to methods of preventing or delaying cognitive decline in a human or animal patient in need thereof, one such method comprising administering to the patient an effective amount of a multi-component formulation comprising methylsulfonylmethane, fructose 1,6-diphosphate, and at least one of trehalose, green tea extract, ashwagandha, and rutin. In certain instances, the multi-component formulation comprises just one of trehalose, green tea extract, ashwagandha, and rutin.

Additional embodiments relate to methods of preventing or delaying AD or other dementia in a human or animal patient in need thereof, one such method comprising administering to the patient an effective amount of a multi-component formulation comprising methylsulfonylmethane, fructose 1,6-diphosphate, and at least one of trehalose, green tea extract, ashwagandha, and rutin. In certain instances, the multi-component formulations comprise just one of trehalose, green tea extract, ashwagandha, and rutin.

Yet other embodiments relate to methods of treating cognitive decline in a human or animal patient in need thereof, comprising administering to the patient an effective amount of a multi-component formulation comprising methylsulfonylmethane, fructose 1,6-diphosphate, and at least one of trehalose, green tea extract, ashwagandha, and rutin. In certain instances, the multi-component formulation comprises just one of trehalose, green tea extract, ashwagandha, and rutin.

Still additional embodiments relate to methods of treating AD or other dementia in a human or animal patient in need thereof, comprising: administering to the patient an effective amount of the multi-component formulation comprising methylsulfonylmethane, fructose 1,6-diphosphate, and at least one of trehalose, green tea extract, ashwagandha, and rutin. In certain instances, the multi-component formulation comprises just one of trehalose, green tea extract, ashwagandha, and rutin.

Yet further additional embodiments provide methods of making the multi-component formulation of any one of the preceding claims, one such method comprising combining methylsulfonylmethane, fructose 1,6-diphosphate, and at least one of trehalose, green tea extract, ashwagandha, and rutin into a form suitable for administration to a human or animal patient in need thereof. In certain instances, the multi-component formulation comprises just one of trehalose, green tea extract, ashwagandha, and rutin.

While the disclosure provides certain specific embodiments, the invention is not limited to those embodiments. A person of ordinary skill will appreciate from the description herein that modifications can be made to the described embodiments and therefore that the specification is broader in scope than the described embodiments. All examples are therefore non-limiting.

DETAILED DESCRIPTION

Figure 1:
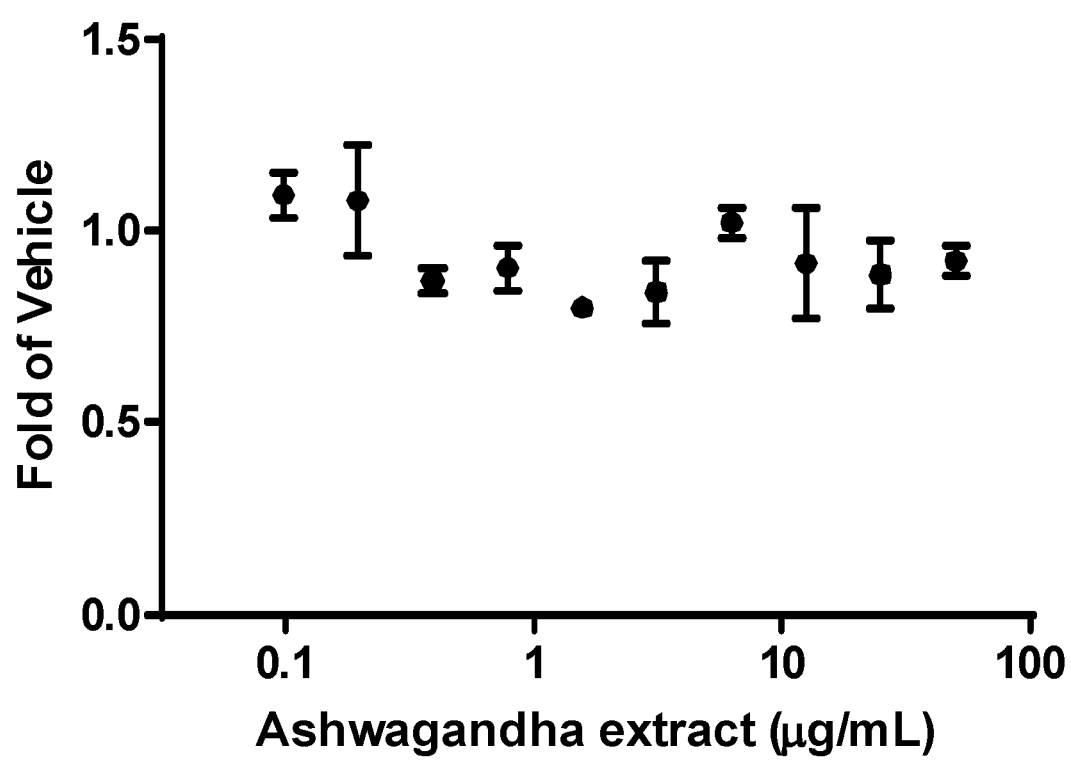
FIG. 1 depicts the effect on cell viability of human neural stem cell derived neurons of a composition comprising methylsulfonylmethane, fructose 1,6-diphosphate, and ashwagandha.

As required, detailed embodiments of the present invention are disclosed herein; however, it is to be understood that the disclosed embodiments are merely exemplary of the invention that may be embodied in various forms. The figures are not necessarily to scale, and some features may be exaggerated to show details of particular components. Therefore, specific structural and functional details disclosed herein are not to be interpreted as limiting, but merely as a basis for the claims and as a representative basis for teaching one skilled in the art to variously employ the present invention.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where ever the phrase "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that don't negatively impact the intended purpose. Descriptive terms are understood to be modified by the term "substantially" even if the word "substantially" is not explicitly recited.

The term "about" when used in connection with a numerical value refers to the actual given value, and to the approximation to such given value that would reasonably be inferred by one of ordinary skill in the art, including approximations due to the experimental and or measurement conditions for such given value.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Any discussion of the prior art throughout the specification should in no way be considered as an admission that such prior art is widely known or forms part of common general knowledge in the field.

It is an object of the present invention to overcome or ameliorate at least one of the disadvantages of the prior art, or to provide a useful alternative.

In view of the numerous and substantial benefits to be realized from formulations exhibiting efficacy in the prevention, delay, and treatment of one or more of the wide variety of degenerative effects which accompany AD, the present invention is directed to unique new multi-component formulations for the prevention, delay, and/or treatment of AD, cognitive decline, and/or other neurodegenerative diseases, which counters the multiple contributing factors to AD, cognitive decline, and/or other neurodegenerative diseases, with a novel combination of complementary remedies.

The complementary components combine drugs and herbals, Eastern and Western thinking, natural molecules and nutrients. All of the components of the present formulation, individually and together, work with the body and brain in order to help the body and brain themselves prevent AD. The present formulation should be combined with proper diet, sleep, exercise without stress, also the best regulator of insulin sensitivity, and social/mental/spiritual outlook and lifestyle, including building up "cognitive reserve," in order to minimize the uniquely human and degenerative nature of AD. Although the human brain makes up only 2 percent of the body's mass, it is an organ of amazing complexity and design which controls the entire body. It has virtually no stored oxygen or glucose, and consumes 20 percent of the body's oxygen and 25 percent of the body's glucose, its sole source of energy. As a result, the human brain is continually on the brink of hypoxia and has an enormous and constant appetite for blood and energy, specifically, as much as 15 percent of the blood and 25 percent of the body's essential energy supply at any moment. Oxygen-glucose deprivation then leads to mitochondrial dysfunction and stimulation of neuroprotective proteins. Many of the pathologic characteristics of AD—inflammation, oxidative stress, impaired cerebral blood flow and glucose utilization—result from body imbalances, including stress, obesity, and an overloaded immune system.

Certain formulations of the present invention can help to restore the body's proper balance, and proper lifestyle can help to maintain that balance. The present invention provides a multi-component formulation for the prevention, delay, and/or treatment of AD, cognitive decline, and/or other neurodegenerative diseases.

As stated above, certain embodiments of the present invention relate to a multi-component formulation comprising: methylsulfonylmethane, fructose 1,6-diphosphate, and just one or more than one of trehalose, green tea extract, ashwagandha, and rutin. Any suitable composition can be used as the formulations of the present invention. The term formulation shall include liquids, semi-liquids, colloidal solutions, dispersions, emulsions, microemulsions, and nanoemulsions, including oil-in-water emulsions and water-in-oil emulsions, pastes, powders, and suspensions. The formulations of the present invention may also be included, or packaged, with other non-toxic compounds, such as cosmetic carriers, excipients, binders and fillers, and the like. Specifically, the acceptable cosmetic carriers, excipients, binders, and fillers contemplated for use in the practice of the present invention are those which render the compounds amenable to oral delivery and/or provide stability such that the formulations of the present invention exhibit a commercially acceptable storage shelf life.

Certain instances of the present invention relate to methods of making the multi-component formulations described herein, one such method comprising combining the methylsulfonylmethane, fructose 1,6-diphosphate, and the at least one of trehalose, green tea extract, ashwagandha, and rutin into a form suitable for administration to a human or animal patient in need thereof. The compositions of the invention can be brought into forms suitable for administration by means of usual processes optionally using auxiliary substances such as liquid or solid, powdered ingredients, such as the pharmaceutically customary liquid or solid fillers and extenders, solvents, emulsifiers, lubricants, flavorings, colorings and/or buffer substances. Frequently used auxiliary substances include magnesium carbonate, titanium dioxide, lactose, saccharose, sorbitol, mannitol and other sugars or sugar alcohols, talc, lactoprotein, gelatin, starch, amylopectin, cellulose and its derivatives, animal and vegetable oils such as fish liver oil, sunflower, groundnut or sesame oil, polyethylene glycol and solvents such as, for example, sterile water and mono- or polyhydric alcohols such as glycerol, as well as with disintegrating agents and lubricating agents such as magnesium stearate, calcium stearate, sodium stearyl fumarate and polyethylene glycol waxes. The mixture may then be processed into granules or pressed into tablets.

The active ingredients may be separately premixed with the other non-active ingredients, before being mixed to form a formulation. The active ingredients may also be mixed with each other, before being mixed with the non-active ingredients to form a formulation.

Soft gelatin capsules may be prepared with capsules containing a mixture of the active ingredients of the invention, and optionally vegetable oil, fat, or other suitable vehicle for soft gelatin capsules. Hard gelatin capsules may contain granules of the active ingredients. Hard gelatin capsules may also contain the active ingredients together with solid powdered ingredients such as lactose, saccharose, sorbitol, mannitol, potato starch, corn starch, amylopectin, cellulose derivatives or gelatin.

Liquid preparations may be prepared in the form of syrups, elixirs, concentrated drops or suspensions, e.g. solutions or suspensions containing the active ingredients and the remainder consisting, for example, of sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents. Liquid preparations may also be prepared in the form of a dry powder, reconstituted with a suitable solvent prior to use. Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation, reconstituted with a suitable solvent before use.

Certain embodiments comprise methylsulfonylmethane, fructose 1,6-diphosphate, and trehalose, and no other active ingredient. Other embodiments comprise methylsulfonylmethane, fructose 1,6-diphosphate, and green tea extract, and no other active ingredient. Yet additional embodiments comprise methylsulfonylmethane, fructose 1,6-diphosphate, and ashwagandha, and no other active ingredient. Still other embodiments comprise methylsulfonylmethane, fructose 1,6-diphosphate, and rutin, and no other active ingredient.

Methylsulfonylmethane, fructose 1,6-diphosphate, trehalose, green tea extract, ashwagandha, and rutin have the broadest suitable meanings as understood by one of ordinary skill in the art. Methylsulfonylmethane, $(CH_3)_2SO_2$, is also known as dimethyl sulfone. Fructose 1,6-diphosphate is also known as fructose 1,6-bisphosphate. Any suitable cations can be used to satisfy the negative charges centered on the phosphate groups, such as, for example, protons, alkali metal cations, alkaline earth metal cations, transition metal cations, nitrogen-containing cations, and combinations thereof. The naturally-occurring enantiomer appears in some embodiments of the present invention. D-fructose 1,6-diphosphate trisodium salt hydrate can be mentioned for some embodiments. Trehalose is the disaccharide also known as mycose and tremalose. D-(+)-trehalose anhydrous can be mentioned in certain instances. Green tea extract indicates any substance extracted from the leaves or any portion of the *Camellia sinensis* plant by any suitable methods. Fresh or dried leaves can be ground, immersed in any suitable solvent such as water, ethanol, or the like, brought to reflux, and then the solvent can be evaporated, leaving a green tea extract, for example. The naturally-occurring enantiomer appears in certain embodiments of the present invention. Ashwagandha refers to any portion or extract from the plant *Withania somnifera*. Roots and extracts thereof are mentioned. Rutin is also known as quercetin-3-O-rutinoside. The naturally-occurring enantiomer appears in further embodiments of the present invention. Rutin trihydrate can be mentioned for certain embodiments.

The active ingredients can be present in the multi-component formulations in any suitable amount. In some cases, for example, methylsulfonylmethane comprises at least 0.01%, 0.01% to 0.5%, 0.5% to 1.0%, 1.0% to 5.0%, 5.0% to 10%, 10% to 20%, 20% to 50%, 50% to 75%, 75% to 95%, or less than 99% by weight of the formulation. In other cases, fructose 1,6-diphosphate comprises at least 0.01%, 0.01% to 0.5%, 0.5% to 1.0%, 1.0% to 5.0%, 5.0% to 10%, 10% to 20%, 20% to 50%, 50% to 75%, 75% to 95%, or less than 99% by weight of the formulation. Additional cases provide trehalose in at least 0.01%, 0.01% to 0.5%, 0.5% to 1.0%, 1.0% to 5.0%, 5.0% to 10%, 10% to 20%, 20% to 50%, 50% to 75%, 75% to 95%, or less than 99% by weight of the formulation. In yet further cases, green tea extract is present as at least 0.01%, 0.01% to 0.5%, 0.5% to 1.0%, 1.0% to 5.0%, 5.0% to 10%, 10% to 20%, 20% to 50%, 50% to 75%, 75% to 95%, or less than 99% by weight of the formulation. Yet other cases provide ashwagandha as at least 0.01%, 0.01% to 0.5%, 0.5% to 1.0%, 1.0% to 5.0%, 5.0% to 10%, 10% to 20%, 20% to 50%, 50% to 75%, 75% to 95%, or less than 99% by weight of the formulation. Further additional cases provide rutin in an amount of at least 0.01%, 0.01% to 0.5%, 0.5% to 1.0%, 1.0% to 5.0%, 5.0% to 10%, 10% to 20%, 20% to 50%, 50% to 75%, 75% to 95%, or less than 99% by weight of the formulation.

Some embodiments of the present invention relate to preventing, delaying, or treating cognitive decline or AD in a human or animal patient in need thereof. Those methods comprise administering to the patient an effective amount of the multi-component formulations described herein. Any suitable effective amount can be employed. As used herein, "effective amount" means the amount necessary to render the desired therapeutic result. For example, an effective amount is a level effective to treat, cure, or alleviate the symptoms of a disorder for which the therapeutic compound, biologic or composition is being administered. Amounts effective for the particular therapeutic goal sought will depend upon a variety of factors including the disorder being treated and its severity and/or stage of development/progression; the bioavailability, and activity of the specific compound or formulation used; the route or method of administration and introduction site on the subject; the rate of clearance of the specific compound or biologic and other pharmacokinetic properties; the duration of treatment; inoculation regimen; drugs used in combination or coincident with the specific composition or formulation; the age, body weight, sex, diet, physiology and general health of the subject being treated; and like factors well known to one of skill in the relevant scientific art. Some variation in dosage will necessarily occur depending upon the condition of the patient being treated, and the physician or other individual administering treatment will, in any event, determine the appropriate dose for an individual patient. Thus, it is not useful to specify an exact effective amount in advance. However, in some cases, a dose of a multi-component formulation according to the present invention can be on the order of less than 10 µg, about 10 µg, about 100 µg, about 1 mg, about 10 mg, about 100 mg, about 250 mg, about 500 mg, about 1 g, or more than 1 g.

As used herein, the term "administering" refers to providing a therapeutically effective amount of a formulation or pharmaceutical composition to a subject, using intravitreal, intraocular, ocular, subretinal, intrathecal, intravenous, subcutaneous, transcutaneous, intracutaneous, intracranial, topical and the like administration. The formulation or pharmaceutical compound of the present invention can be administered alone, but may be administered with other compounds, excipients, fillers, binders, carriers or other vehicles selected based upon the chosen route of administration and standard pharmaceutical practice. Administration may be by way of carriers or vehicles, such as injectable solutions, including sterile aqueous or non-aqueous solutions, or saline solutions; creams; lotions; capsules; tablets; granules; pellets; powders; suspensions, emulsions, or microemulsions; patches; micelles; liposomes; vesicles; implants, including microimplants; eye drops; other proteins and peptides; synthetic polymers; microspheres; nanoparticles; and the like.

The formulations or pharmaceutical composition of the present invention may also be included, or packaged, with other non-toxic compounds, such as pharmaceutically acceptable carriers, excipients, binders and fillers including, but not limited to, glucose, lactose, gum acacia, gelatin, mannitol, xanthan gum, locust bean gum, galactose, oligosaccharides and/or polysaccharides, starch paste, magnesium trisilicate, talc, corn starch, starch fragments, keratin, colloidal silica, potato starch, urea, dextrans, dextrins, and the like. Specifically, the pharmaceutically acceptable carriers, excipients, binders, and fillers contemplated for use in the practice of the present invention are those which render the compounds of the invention amenable to intravitreal delivery, intraocular delivery, ocular delivery, subretinal delivery, intrathecal delivery, intravenous delivery, subcutaneous delivery, transcutaneous delivery, intracutaneous delivery, intracranial delivery, topical delivery and the like. Moreover, the packaging material may be biologically inert or lack bioactivity, such as plastic polymers, silicone, etc. And may be processed internally by the subject without affecting the effectiveness of the composition/formulation packaged and/or delivered therewith.

As used herein, "treatment" or "treating" refers to arresting or inhibiting, or attempting to arrest or inhibit, the progression of a disorder and/or causing, or attempting to cause, the reduction, suppression, regression, or remission of a disorder and/or a symptom thereof. As would be understood by those skilled in the art, various clinical and scientific methodologies and assays may be used to assess the development or progression of a disorder, and similarly, various clinical and scientific methodologies and assays may be used to assess the reduction, regression, or remission of a disorder or its symptoms.

As used herein, "prevention" or "preventing" refers to arresting or inhibiting, or attempting to arrest or inhibit, the initial onset or development of a disorder. The prevention of a disorder may occur before any clinical signs of the disorder being prevented are recognized.

In one embodiment, the disorder being treated, delayed, and/or prevented by the formulations and compositions of the present invention is a neurodegenerative disease, such as dementia or cognitive decline, which includes at least AD.

The many contributing factors to AD, together with each individual's unique makeup, genetic and otherwise, create a mind-boggling number of combinations which the present multi-component formulation is uniquely qualified to counter. If one component does not work with a particular individual, another component may. The multiple synergies between the different components of the present formulation increase the opportunity for at least one such synergy to provide an effective treatment for a particular person, unlike conventional single component drugs, which fail to benefit one in three patients and make one in seven to eight worse.

Different forms of the present inventive formulation can be calibrated in order to adapt both to different individuals and to the different needs of a single individual. Implementing this concept is complicated, and the necessary research is challenging. However, the present formulation need not counter every cause in every individual. Rather, by countering the necessary causes, the present formulation will restore the body and brain to their normal function. Then the body and brain themselves will correct the remaining deficiencies. No drug can possibly correct every single cause of AD, but the present formulation will maximize the possibility.

The end result of the present inventive formulation is to push back the threshold age of development of AD or cognitive decline, i.e., to delay or prevent the onset of AD until later in life, or alternatively, to eliminate AD or cognitive decline altogether for some people. The formulation is not expected to be a cure for advanced AD. AD has a lengthy, non-linear, accelerating, and degenerative prodromal time period with ample opportunity for preventive intervention. Approximately 95% of AD cases are sporadic late-onset. The inventive formulation should be combined with early detection of mild cognitive impairment (MCI) and cognitive impairment which is not dementia (CIND), conditions that may develop into AD, in order to maximize its effectiveness. MCI/CIND is a fluid, non-homogeneous, and unstable state, which is a critical time to intervene. The inventive formulation may be marketed to all people over 50 as a preventive measure, including those with no cognitive impairment. A 5-year delay of the onset of AD would yield spectacular results.

Testing of formulations of the present invention can be performed in accordance with any suitable protocol. Some such testing could be focused on maximizing the exogenous stimulation of endogenous neuroprotective proteins, mild stress-induced hormesis, inhibiting the production of reactive oxygen species, restoring homeostasis, and on examining the interrelationships and synergies between such neuroprotective proteins, the immune system, DNA (including SIRT1), epigenetics, cell senescence, neurogenesis, and neurodegeneration.

Without further elaboration, it is believed that one skilled in the art can utilize the present invention to its fullest extent based on the disclosure herein. The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

EXAMPLES

Example 1—Cell Viability of Human Stem Cell Derived Neurons Treated with Multi-Component Formulations Cryopreserved human stem cell derived neurons obtained from PhoenixSongs Biologicals were thawed and plated at a density of 12000 cells per well in a 384-well PDL/laminin coated plate. The neurons were maintained in a humidified environment at 37° C. with 5% $CO_2$ for six days with periodic media changes before experimental procedures were performed. The media used for maintenance and dosing was PhoenixSongs Neural Differentiation Medium and for the survival test contained methylsulfonylmethane ("MSM") and fructose 1,6-diphosphate ("FDP") (specifically, D-fructose 1,6-diphosphate trisodium salt hydrate) with final concentrations of 0.1 µM and 1 µM, respectively. Cells were dosed in triplicate with 10-point dose response curves to determine if there was any protective effect (improved survival of cells) or toxicity with the test compounds versus the untreated cells. A positive control (chlorpromazine) was also used to assess cytotoxicity response in these cells.

Figure 2:
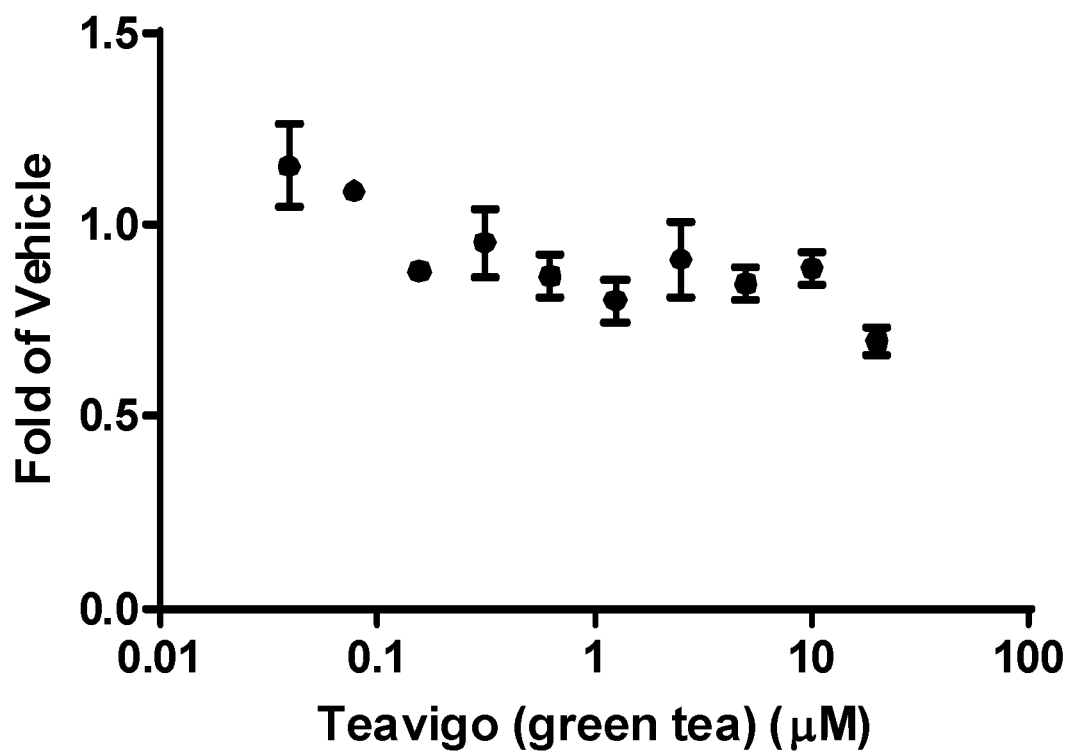
FIG. 2 depicts the effect on cell viability of human neural stem cell derived neurons of a composition comprising methylsulfonylmethane, fructose 1,6-diphosphate, and green tea extract.
Figure 3:
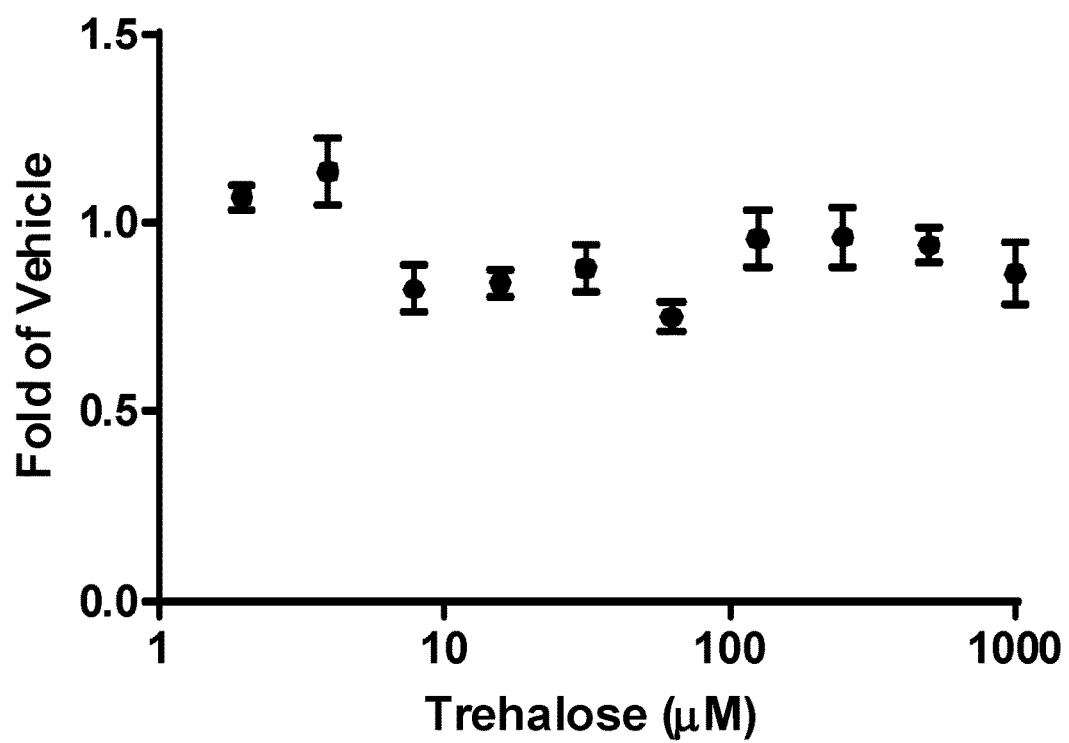
FIG. 3 depicts the effect on cell viability of human neural stem cell derived neurons of a composition comprising methylsulfonylmethane, fructose 1,6-diphosphate, and trehalose.
Figure 4:
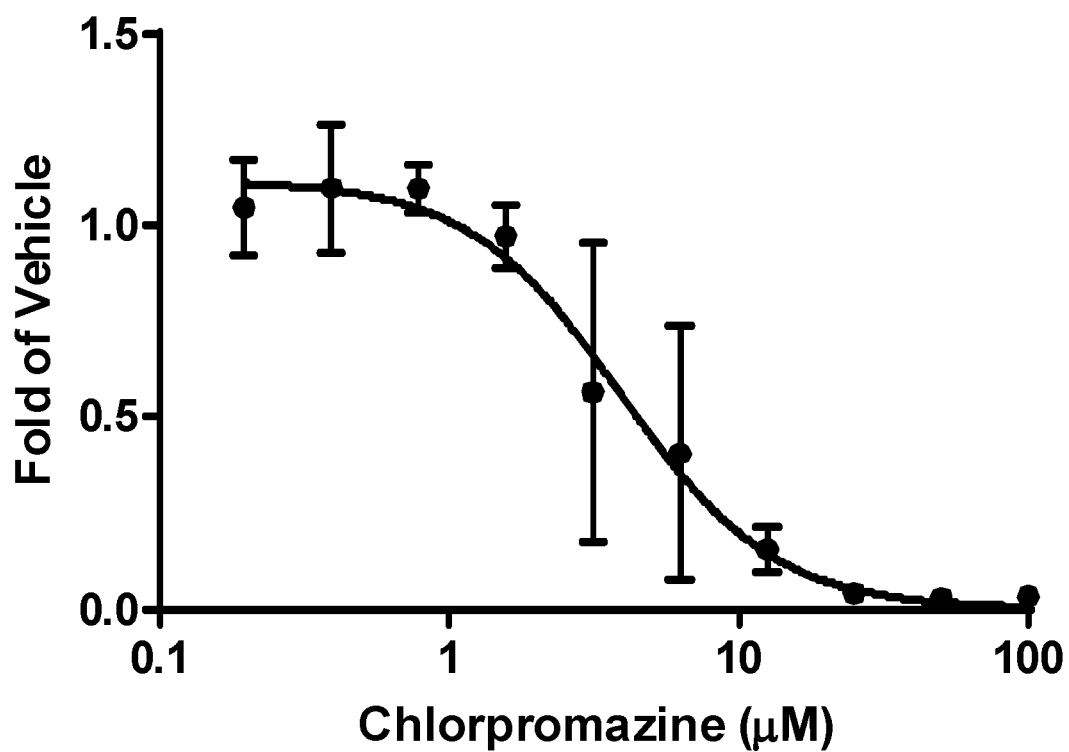
FIG. 4 depicts the effect on cell viability of human neural stem cell derived neurons of a composition comprising chlorpromazine.

After a three-day incubation with test compositions, the cells were stained with Hoechst and propidium iodide and read on an ArrayScan VTI to determine cell viability. Results were normalized to vehicle and graphed using GraphPad Prism. FIG. 1 shows the dose response curve for ashwagandha; FIG. 2 shows the dose response curve for green tea extract known as Teavigo (90% purity); FIG. 3 shows the dose response curve for D-(+)-trehalose anhydrous; and FIG. 4 shows the dose response curve for chlorpromazine (without methylsulfonylmethane and fructose 1,6-diphosphate). IC50 values appear in Table 1 below:

TABLE 1

| Formulation | $IC_{50}$ for Cell Loss |
|---|---|
| MSM + FDP + Ashwagandha | >50 µg/mL |
| MSM + FDP + Green Tea Extract | >20 µM |
| MSM + FDP + Trehalose | >1000 µM |
| Chlorpromazine | 3.8 µM |

Chlorpromazine is used as an antipsychotic in spite of its relatively high neuron cell toxicity as shown in this study. The inventive compositions are shown to be much safer at comparable concentrations than the standard antipsychotic compound.

Example 2—Cell Viability of Primary Chicken Neurons Treated with Rutin

Fertilized chicken eggs were stored under turning at 37.8° C. and 55% humidity until embryonic day eight. Embryos were transferred to a plastic dish and decapitated. Both hemispheres were removed, collected and cleaned from any loose tissue. Hemispheres were mechanically dissociated and $4.8 \times 10^4$ cells per well (96-well plates) were seeded in a volume of 160 µL. The cell culture medium consisted of Dubelcco's Modified Eagle's Medium with 4.5 g glucose, 5% Nu Serum, 0.01% gentamycin and 2 mM L-glutamine. Cultures were maintained at 37° C., 95% humidity and 5% $CO_2$.

Test compositions and vehicle controls were applied to chicken neurons at day-in-vitro 8 for 48 h. On day-in-vitro 10 the viability of neurons was determined according to MTT cell viability assay using a plate reader (570 nm). That assay allows the measurement of the mitochondrial dehydrogenase activity, which reduces yellow MTT to dark blue formazan crystals. Since this reaction is catalyzed in living cells only, this assay is used for the determination of cell viability. MTT solution was added to each well in a final concentration of 0.5 mg/mL. After two hours the MTT-containing medium is aspired. Cells were lysed in 3% SDS and the formazan crystals were dissolved in isopropanol/HCl. Optical density was measured with a plate reader at 570 nm. Cell survival rage was expressed as optical density (OS). Values were calculated as percent of control values (vehicle control, which is medium).

Results from administering rutin in vehicle alone appear in Table 2:

TABLE 2

| Rutin | VC | 0.001 | 0.01 | 0.1 | 1 | 10 |
|---|---|---|---|---|---|---|
| Mean | 100.0 | 96.7 | 99.7 | 98.1 | 97.7 | 100.2 |
| Std. Deviation | 3.97 | 6.08 | 8.57 | 4.79 | 7.91 | 9.21 |
| Std. Error | 1.15 | 1.76 | 2.47 | 1.38 | 2.39 | 2.66 |

Application of rutin (with no MSM nor FDP) did not enhance cell viability compared to vehicle-treated cells.

Results from administering MSM, FDP, and rutin appear in Table 3:

TABLE 3

| Rutin + MSM/FDP | VC | MF | 0.001 | 0.01 | 0.1 | 1 | 10 |
|---|---|---|---|---|---|---|---|
| Mean | 100.0 | 97.1 | 108.0 | 103.4 | 104.2 | 100.2 | 104.1 |
| Std. Deviation | 6.37 | 0.01 | 7.04 | 6.48 | 9.60 | 9.89 | 4.45 |
| Std. Error | 1.84 | 3.04 | 2.03 | 1.87 | 2.77 | 2.85 | 1.29 |

A combination of methylsulfonylmethane, fructose 1,6-diphosphate, and rutin at a concentration of 0.001 µM significantly improved cell viability compared to vehicle or MSM/FDP-only treated cells. At other concentrations, MSM/FDP/Rutin improved cell viability compared to MSM/FDP alone in this study.

Example 3—MSM and FDP Alone or Together

Figure 5:
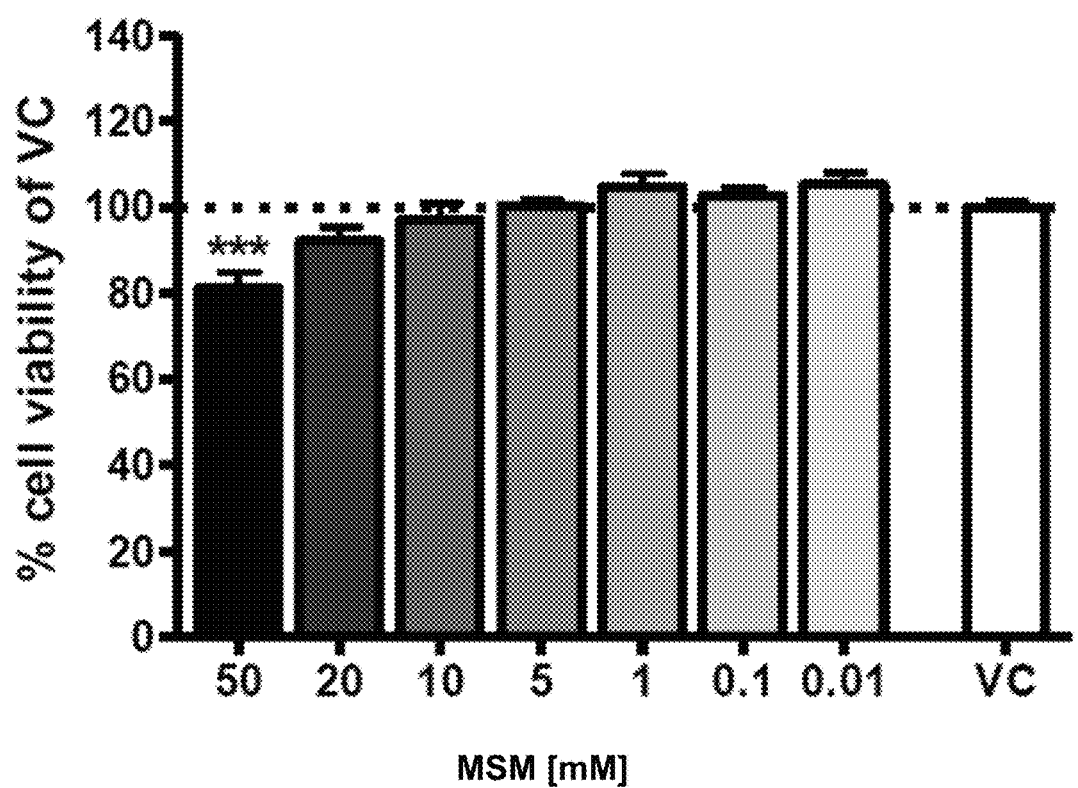
FIG. 5 depicts the effect on cell viability of primary chicken neurons of a composition comprising methylsulfonylmethane.
Figure 6:
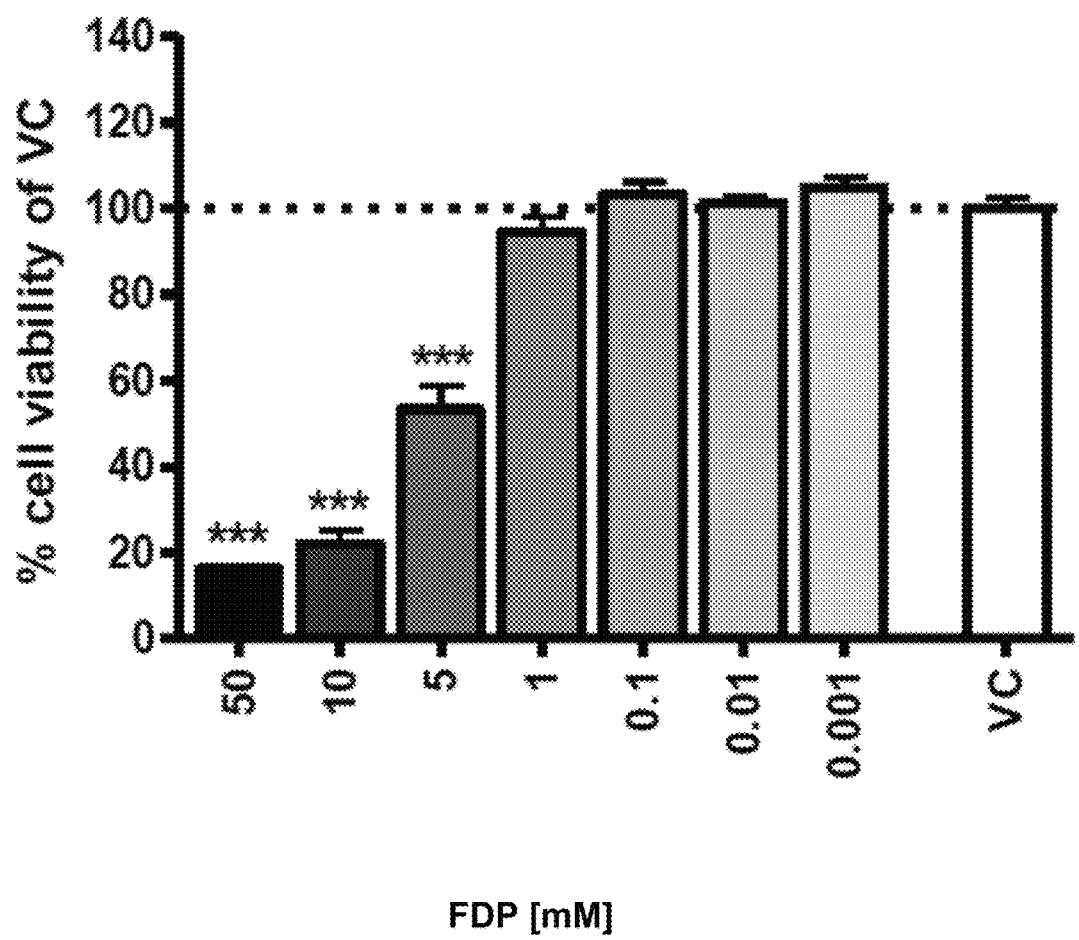
FIG. 6 depicts the effect on cell viability of primary chicken neurons of a composition comprising fructose 1,6-diphosphate.
Figure 7:
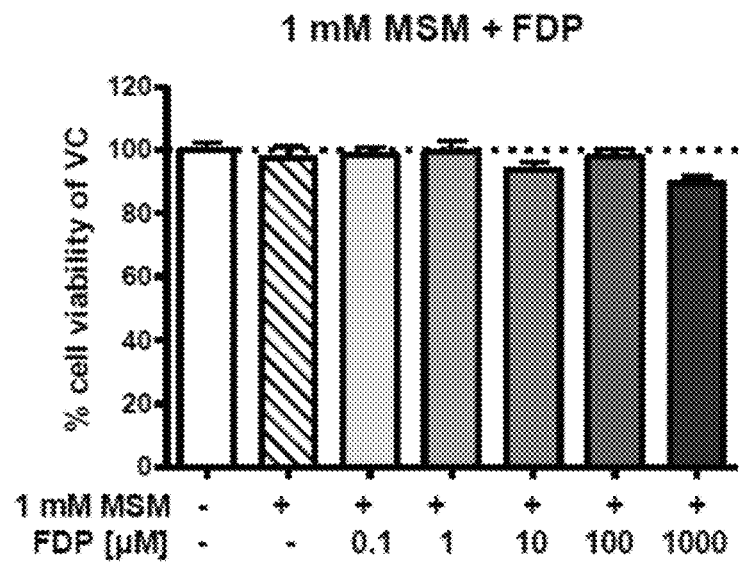
FIG. 7 depicts the effect on cell viability of primary chicken neurons of a composition comprising 1 mM methylsulfonylmethane and varying concentrations of fructose 1,6-diphosphate.
Figure 8:
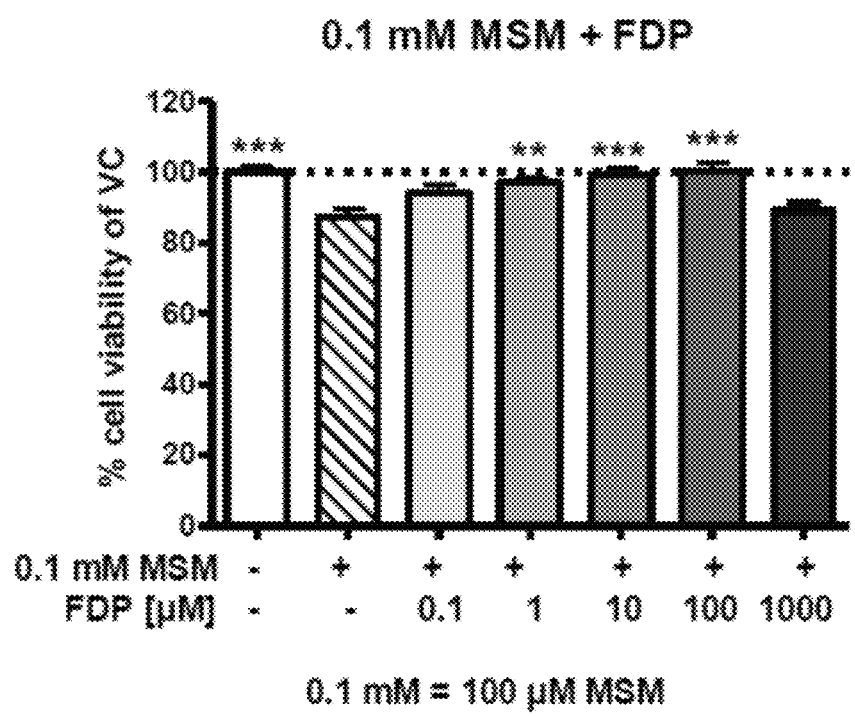
FIG. 8 depicts the effect on cell viability of primary chicken neurons of a composition comprising 0.1 mM methylsulfonylmethane and varying concentrations of fructose 1,6-diphosphate.
Figure 9:
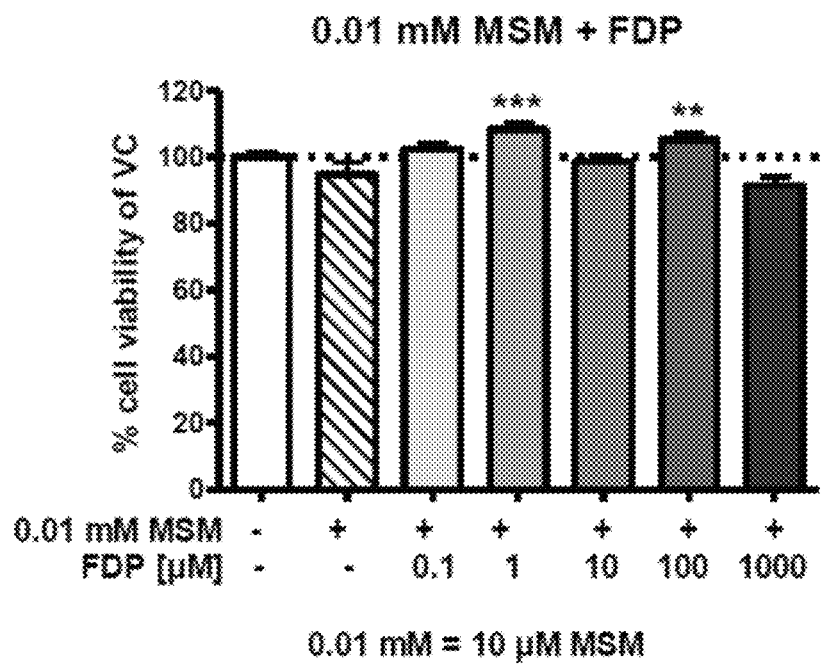
FIG. 9 depicts the effect on cell viability of primary chicken neurons of a composition comprising 0.01 mM methylsulfonylmethane and varying concentrations of fructose 1,6-diphosphate.
Figure 10:
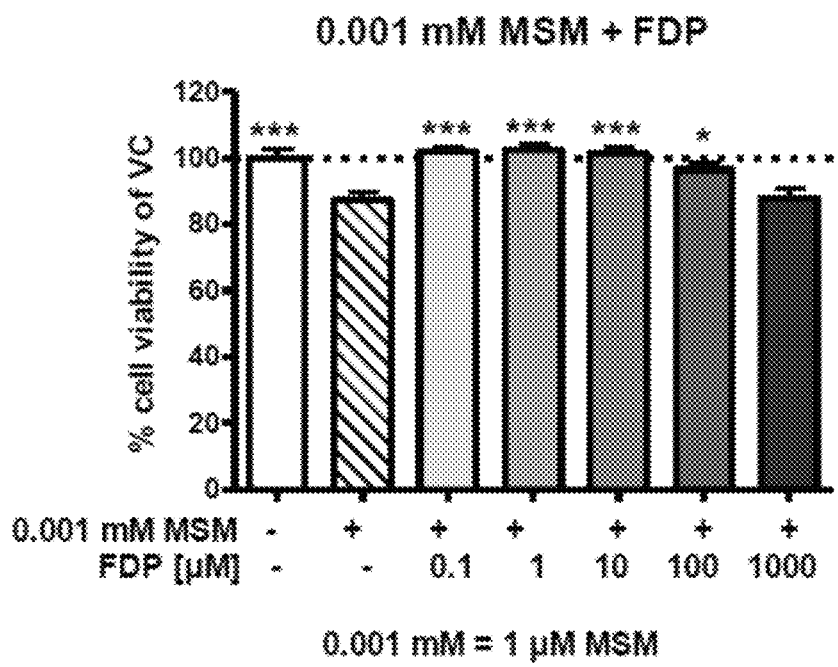
FIG. 10 depicts the effect on cell viability of primary chicken neurons of a composition comprising 0.001 mM methylsulfonylmethane and varying concentrations of fructose 1,6-diphosphate.
Figure 11:
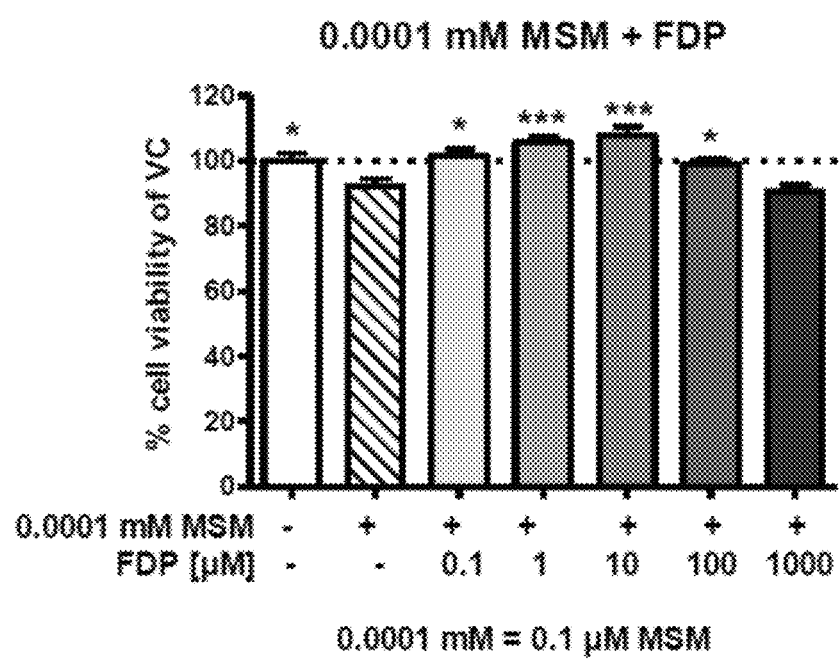
FIG. 11 depicts the effect on cell viability of primary chicken neurons of a composition comprising 0.0001 mM methylsulfonylmethane and varying concentrations of fructose 1,6-diphosphate.

Using the same protocol as in Example 2, primary chicken neurons were treated with varying concentrations of methylsulfonylmethane and/or fructose 1,6-diphosphate. Cell viability was determined with the MTT assay. Compared to vehicle control, FIG. 5 shows that cell viability declined at MSM concentrations above 5 mM. FIG. 6 shows that cell viability declined at FDP concentrations above 0.1 mM.

FIGS. 7-11 compare cell viability at various concentrations of MSM and FDP. White bars represent vehicle (medium), light grey to dark grey bars represent combinations of MSM and FDP in vehicle, and bars with crossed lines represent data for cells treated with just one substance in vehicle. The best combinatorial effects of MSM and FDP were achieved when FDP was chosen at a concentration of 1 µM and MSM at a concentration of 1 and 0.1 µM.

Example 4—Cell Viability of Primary Chicken Neurons Treated with Rutin

Figure 12:
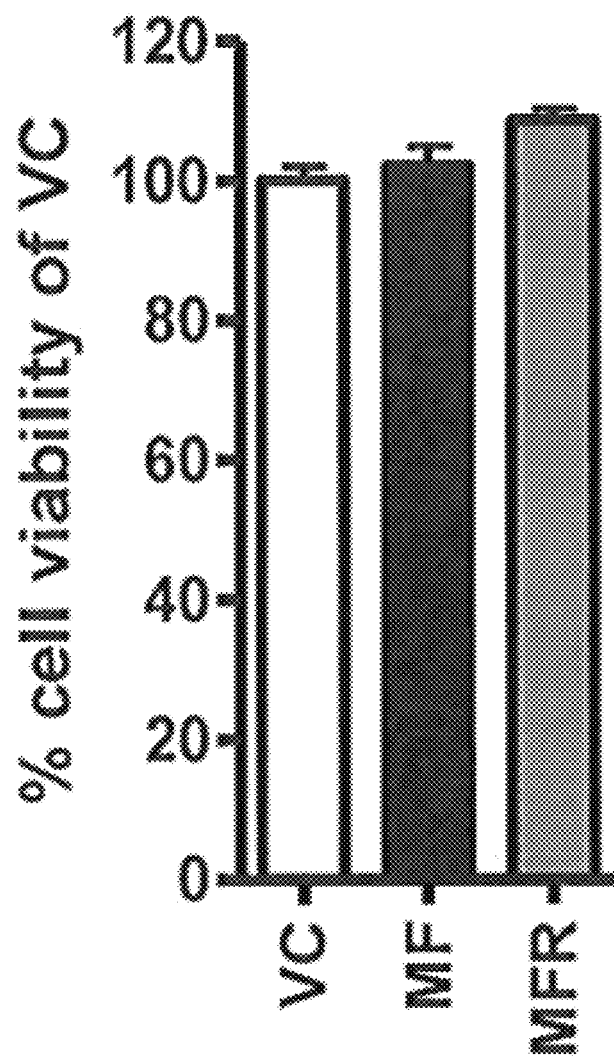
FIG. 12 depicts the effect on cell viability of primary chicken neurons of compositions comprising a vehicle control ("VC"), methylsulfonylmethane and fructose 1,6-diphosphate ("MF"), and methylsulfonylmethane, fructose 1,6-diphosphate, and rutin ("MFR").

Using the protocol of Example 2, a formulation containing methylsulfonylmethane (0.1 µM), D-fructose 1,6-diphosphate trisodium salt hydrate (1 µM), and rutin (0.001 µM) was tested for cell viability in primary chicken neurons. Vehicle control (medium) and methylsulfonylmethane with fructose 1,6-diphosphate compositions were also tested. The results appear in FIG. 12. The formulation with three active ingredients increased cell viability over vehicle control and MSM+FDP alone, although the increase was not considered statistically significant.

Example 5—Ischemic Challenge

Similar to Example 1, cryopreserved human stem cell derived neurons obtained from PhoenixSongs Biologicals were thawed and plated at a density of 12000 cells per well in a 384-well PDL/laminin coated plate. The neurons were maintained in a humidified environment at 37° C. with 5% $CO_2$ for six days with periodic media changes before experimental procedures were performed. The media used for the experiment was PhoenixSongs Neural Differentiation Medium and contained methylsulfonylmethane ("MSM") and fructose 1,6-diphosphate ("FDP") (specifically, D-fructose 1,6-diphosphate trisodium salt hydrate) with final concentrations of 0.1 µM and 1 µM, respectively, for some cells. The neural differentiation medium optionally with MSM and FDP was spiked with iodoacetic acid (challenge) at 5 µM and was used to challenge the cells for ischemia. Cells with medium and MSM and FDP were dosed in triplicate with 10-point dose response curves to determine if there was any protective effect (improved survival of cells) or toxicity with rutin trihydrate versus the untreated cells.

Figure 13:
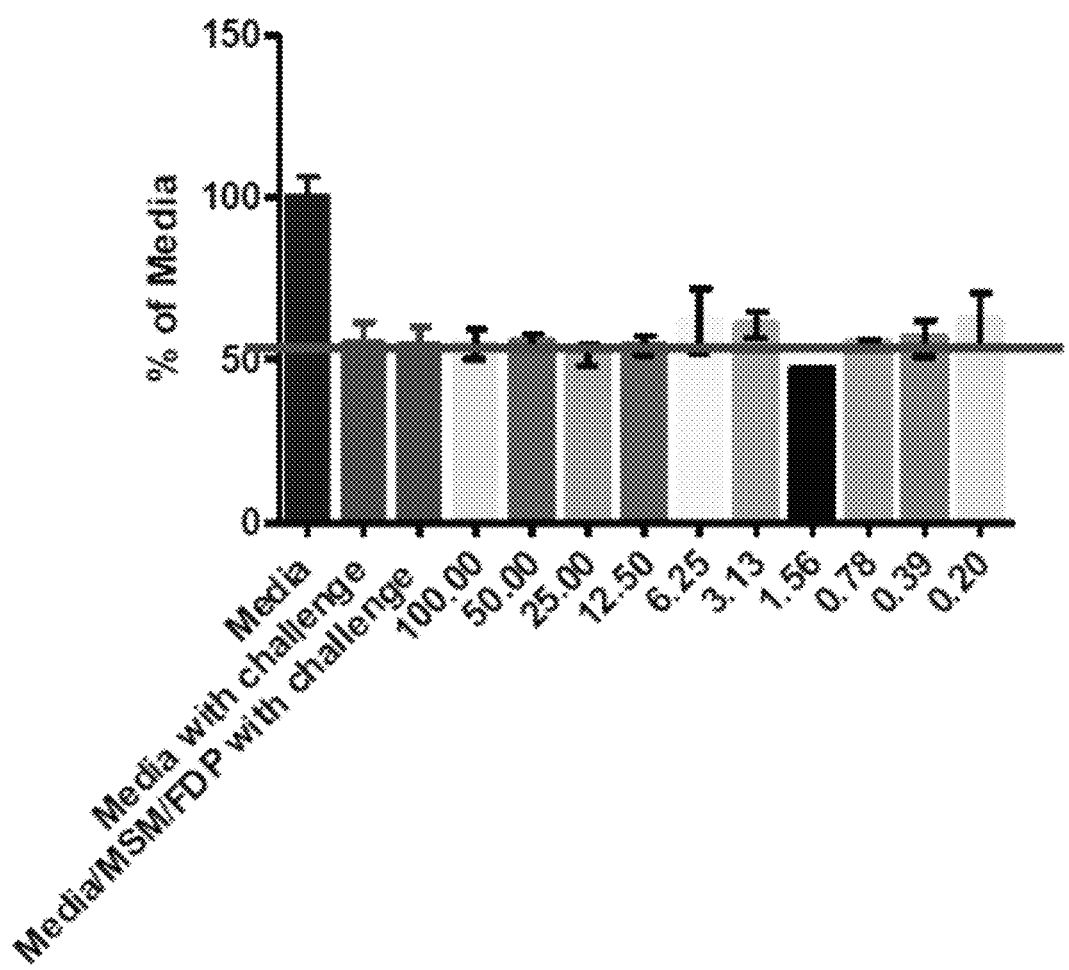
FIG. 13 depicts the effect on cell viability of human neural stem cell derived neurons of various compositions including those containing various concentrations of rutin trihydrate.

After 24-hour incubation with rutin trihydrate and iodoacetic acid, the cells were stained with Hoechst and propidium iodide and read on an ArrayScan VTI to determine cell viability. Results were normalized to vehicle (medium alone) and graphed using GraphPad Prism. Statistical significance was determined by performing a one-way analysis of variance followed by a Dunnett test for comparing every test mean to the mean of the media with challenge. The results for rutin trihydrate at various micromolar concentrations appear in FIG. 13. Several concentrations of rutin trihydrate show improved cell viability compared to media with challenge and media/MSM/FDP with challenge, although were not considered statistically significant.

EMBODIMENTS

Embodiment 1

A multi-component formulation comprising: methylsulfonylmethane,
fructose 1,6-diphosphate, and
at least one of trehalose, green tea extract, ashwagandha, and rutin.

Embodiment 2

The multi-component formulation of embodiment 1, comprising just one of trehalose, green tea extract, ashwagandha, and rutin.

Embodiment 3

The multi-component formulation of embodiment 2, comprising trehalose.

Embodiment 4

The multi-component formulation of embodiment 2, comprising green tea extract.

Embodiment 5

The multi-component formulation of embodiment 2, comprising ashwagandha.

Embodiment 6

The multi-component formulation of embodiment 2, comprising rutin.

Embodiment 7

The multi-component formulation of any one of the preceding embodiments, wherein the methylsulfonylmethane comprises at least 0.01%, 0.01% to 0.5%, 0.5% to 1.0%, 1.0% to 5.0%, 5.0% to 10%, 10% to 20%, 20% to 50%, 50% to 75%, 75% to 95%, or less than 99% by weight of the formulation.

Embodiment 8

The multi-component formulation of any one of the preceding embodiments, wherein the fructose 1,6-diphosphate comprises at least 0.01%, 0.01% to 0.5%, 0.5% to 1.0%, 1.0% to 5.0%, 5.0% to 10%, 10% to 20%, 20% to 50%, 50% to 75%, 75% to 95%, or less than 99% by weight of the formulation.

Embodiment 9

The multi-component formulation of any one of the preceding embodiments, wherein the trehalose, if present, comprises at least 0.01%, 0.01% to 0.5%, 0.5% to 1.0%, 1.0% to 5.0%, 5.0% to 10%, 10% to 20%, 20% to 50%, 50% to 75%, 75% to 95%, or less than 99% by weight of the formulation.

Embodiment 10

The multi-component formulation of any one of the preceding embodiments, wherein the green tea extract, if present, comprises at least 0.01%, 0.01% to 0.5%, 0.5% to 1.0%, 1.0% to 5.0%, 5.0% to 10%, 10% to 20%, 20% to 50%, 50% to 75%, 75% to 95%, or less than 99% by weight of the formulation.

Embodiment 11

The multi-component formulation of any one of the preceding embodiments, wherein the ashwagandha, if present, comprises at least 0.01%, 0.01% to 0.5%, 0.5% to 1.0%, 1.0% to 5.0%, 5.0% to 10%, 10% to 20%, 20% to 50%, 50% to 75%, 75% to 95%, or less than 99% by weight of the formulation.

Embodiment 12

The multi-component formulation of any one of the preceding embodiments, wherein the rutin, if present, comprises at least 0.01%, 0.01% to 0.5%, 0.5% to 1.0%, 1.0% to 5.0%, 5.0% to 10%, 10% to 20%, 20% to 50%, 50% to 75%, 75% to 95%, or less than 99% by weight of the formulation.

Embodiment 13

A method of making the multi-component formulation of any one of the preceding embodiments, comprising: combining the methylsulfonylmethane, fructose 1,6-diphosphate, and the at least one of trehalose, green tea extract, ashwagandha, and rutin into a form suitable for administration to a human or animal patient in need thereof.

Embodiment 14

A method of preventing or delaying cognitive decline in a human or animal patient in need thereof, comprising: administering to the patient an effective amount of the multi-component formulation of any one of embodiments 1-12.

Embodiment 15

A method of preventing or delaying Alzheimer's disease or other dementia in a human or animal patient in need thereof, comprising: administering to the patient an effective amount of the multi-component formulation of any one of embodiments 1-12.

Embodiment 16

A method of treating cognitive decline in a human or animal patient in need thereof, comprising: administering to the patient an effective amount of the multi-component formulation of any one of embodiments 1-12.

Embodiment 17

A method of treating Alzheimer's disease or other dementia in a human or animal patient in need thereof, comprising: administering to the patient an effective amount of the multi-component formulation of any one of embodiments 1-12.

As previously stated, detailed embodiments of the present invention are disclosed herein; however, it is to be understood that the disclosed embodiments are merely exemplary of the invention that may be embodied in various forms. It will be appreciated that many modifications and other variations stand within the intended scope of this invention as claimed below. Furthermore, the foregoing description of various embodiments does not necessarily imply exclusion. For example, "some" embodiments may include all or part of "other" and "further" embodiments within the scope of this invention. In addition, "a" does not mean "one and only one;" "a" can mean "one and more than one."

I claim:
1. A multi-component formulation to improve neuron viability consisting essentially of:
   1.0% to 5.0% by weight methylsulfonylmethane,
   20% to 50% by weight fructose 1,6-diphosphate, and
   one of trehalose, green tea extract, ashwagandha, and rutin, in an amount of at least 0.01% by weight of the formulation.
2. The multi-component formulation of claim 1, comprising trehalose.
3. The multi-component formulation of claim 1, comprising green tea extract.
4. The multi-component formulation of claim 1, comprising ashwagandha.
5. The multi-component formulation of claim 1, comprising rutin.
6. A method of making the multi-component formulation of claim 1, comprising:
   combining the methylsulfonylmethane, fructose 1,6-diphosphate, and the just one of trehalose, green tea extract, ashwagandha, and rutin, into a form suitable for administration to a human or animal patient in need thereof.
7. A method of treating cognitive decline in a human or animal patient in need thereof, comprising:
   administering to the patient in need thereof an effective amount of the multi-component formulation of claim 1.
8. A method of treating Alzheimer's disease or other dementia in a human or animal patient in need thereof, comprising:

administering to the patient in need thereof an effective amount of the multi-component formulation of claim 1.

9. A multi-component formulation to improve neuron viability consisting essentially of:
 1.0% to 5.0% by weight methylsulfonylmethane,
 10% to 20% by weight fructose 1,6-diphosphate, and
 one of trehalose, green tea extract, ashwagandha, and rutin, in an amount of at least 0.01% by weight of the formulation.

10. The multi-component formulation of claim 1, comprising trehalose.

11. The multi-component formulation of claim 1, comprising green tea extract.

12. The multi-component formulation of claim 1, comprising ashwagandha.

13. The multi-component formulation of claim 1, comprising rutin.

\* \* \* \* \*